(12) United States Patent
Vergez et al.

(10) Patent No.: US 8,241,667 B2
(45) Date of Patent: Aug. 14, 2012

(54) DUAL CONTROLLED RELEASE OSMOTIC DEVICE

(75) Inventors: Juan A. Vergez, Buenos Aires (AR); Marcelo A. Ricci, Buenos Aires (AR)

(73) Assignee: Osmotica Kereskedelmi és Szolgáltató KFT, Budapest (HU)

( * ) Notice: Subject to any disclaimer, the term of this patent is extended or adjusted under 35 U.S.C. 154(b) by 1652 days.

(21) Appl. No.: 11/321,736

(22) Filed: Dec. 29, 2005

(65) Prior Publication Data

US 2006/0177510 A1 Aug. 10, 2006

Related U.S. Application Data

(62) Division of application No. 09/992,488, filed on Nov. 6, 2001, now abandoned.

(51) Int. Cl.
*A61K 9/24* (2006.01)

(52) U.S. Cl. ..................................... 424/473

(58) Field of Classification Search ................... None
See application file for complete search history.

(56) References Cited

U.S. PATENT DOCUMENTS

| | | | |
|---|---|---|---|
| 4,111,202 A | 9/1978 | Theeuwes | |
| 4,309,996 A | 1/1982 | Theeuwes | |
| 4,327,725 A | 5/1982 | Cortese et al. | |
| 4,449,983 A * | 5/1984 | Cortese et al. | 604/892.1 |
| 4,455,143 A | 6/1984 | Theeuwes | |
| 4,612,008 A | 9/1986 | Wong et al. | |
| 4,624,847 A | 11/1986 | Ayer et al. | |
| 4,627,971 A | 12/1986 | Ayer | |
| 4,662,880 A | 5/1987 | Hamel et al. | |
| 4,681,583 A | 7/1987 | Urquhart et al. | |
| 4,723,957 A | 2/1988 | Magruder et al. | |
| 4,765,989 A | 8/1988 | Wong et al. | |
| 4,814,181 A * | 3/1989 | Jordan et al. | 424/473 |
| 4,863,456 A | 9/1989 | Stephens et al. | |
| 4,867,969 A | 9/1989 | Magruder et al. | |
| 4,904,474 A | 2/1990 | Theeuwes et al. | |
| 4,915,954 A | 4/1990 | Ayer et al. | |
| 4,931,285 A | 6/1990 | Edgren et al. | |
| 4,960,416 A | 10/1990 | Stephens et al. | |
| 4,971,790 A | 11/1990 | Magruder et al. | |
| 5,006,346 A | 4/1991 | Edgren et al. | |
| 5,082,668 A | 1/1992 | Wong et al. | |
| 5,160,743 A | 11/1992 | Edgren et al. | |
| 5,160,744 A | 11/1992 | Jao et al. | |
| 5,190,765 A | 3/1993 | Jao et al. | |
| 5,208,037 A | 5/1993 | Wright et al. | |
| 5,236,689 A * | 8/1993 | Wong et al. | 424/473 |
| 5,252,338 A | 10/1993 | Jao et al. | |
| 5,399,359 A | 3/1995 | Baichwal | |
| 5,543,155 A | 8/1996 | Fekete et al. | |
| 5,674,895 A | 10/1997 | Guittard et al. | |
| 5,788,987 A | 8/1998 | Busetti et al. | |
| 5,840,754 A | 11/1998 | Guittard et al. | |
| 5,866,164 A | 2/1999 | Kuczynski et al. | |
| 5,912,268 A | 6/1999 | Guittard et al. | |
| 6,004,582 A * | 12/1999 | Faour et al. | 424/473 |
| 6,106,864 A | 8/2000 | Dolan et al. | |
| 6,207,191 B1 * | 3/2001 | Crison et al. | 424/472 |
| 2002/0010216 A1 | 1/2002 | Rogosky et al. | |
| 2006/0204578 A1 | 9/2006 | Vergez | |

FOREIGN PATENT DOCUMENTS

| | | |
|---|---|---|
| JP | 2646170 | 8/1997 |
| JP | 2665658 | 10/1997 |
| WO | 96/12477 | 5/1996 |
| WO | 97/16814 | 5/1997 |
| WO | 00/12069 | 3/2000 |
| WO | 00/19997 | 4/2000 |

OTHER PUBLICATIONS

Dmochowski, R. et al., Advancements in Pharmacologic Management of the Overactive Bladder, Urology, Dec. 2000, vol. 56 (Supplement 6A), 41-49.
Appell, R.A. et al., Clinical Evaluation of a Sustained-Release Form of Oxybutynin (Ditropan SR) for the Treatment of Detrusor Hyperreflexia in Neuropathic Patients, Urodynamics Society Symposium Abstracts, 1990, 228.
Sirkia, T. et al., use of Hydrophilic Polymers to Control Drug Release from Press-Coated Oxybutynin Hydrochloride Tablets, S.T.P. Pharmacia Sci., 1993, 21, 3-8.
Nilsson, C. G. et al., Comparison of a 10-mg Controlled Release Oxybutynin Tablet with a 5-mg Oxybutynin Tablet in Urge Incontinent Patients, 1997, 16:533-542.

* cited by examiner

*Primary Examiner* — David J Blanchard
*Assistant Examiner* — Tigabu Kassa
(74) *Attorney, Agent, or Firm* — Rick Matos; Innovar, L.L.C.

(57) ABSTRACT

A pharmaceutical composition and dosage form for the treatment of incontinence with oxybutynin and a second drug is provided. The second drug can be darifenacin or tolterodine. Depending upon the route of administration, the dosage form used, and the second drug used, the dosage form may independently include therapeutic or sub-therapeutic amounts of the oxybutynin and the second drug. Particular embodiments include a dosage form that provides a controlled release of oxybutynin and the second drug to maintain therapeutically effective levels oxybutynin and/or the second in a mammal for an extended period of time. An osmotic device containing a bi-layered core is provided. The osmotic device provides a dual controlled release of both drugs from the core. A method of treating urinary (stress or urge) incontinence with the pharmaceutical composition and dosage form is provided. Together, oxybutynin and the second drug provide an overall improved therapeutic benefit over either agent alone when administered at approximately the same dose.

51 Claims, 3 Drawing Sheets

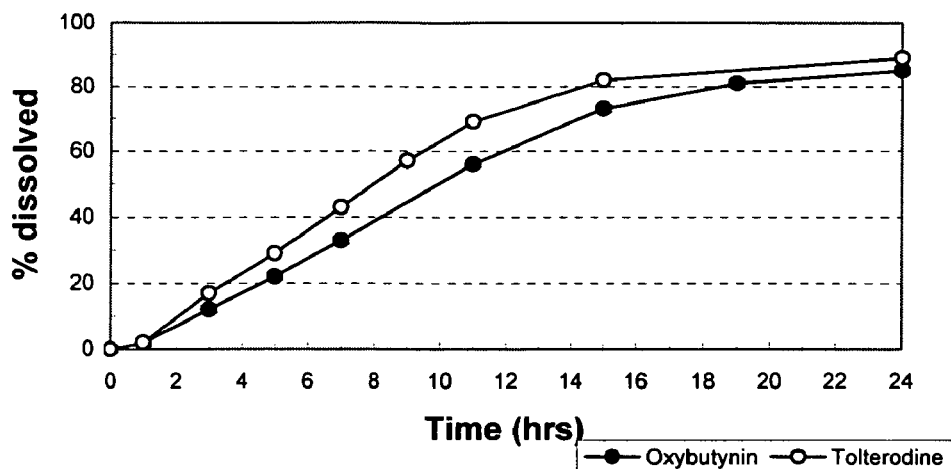
FIG. 7
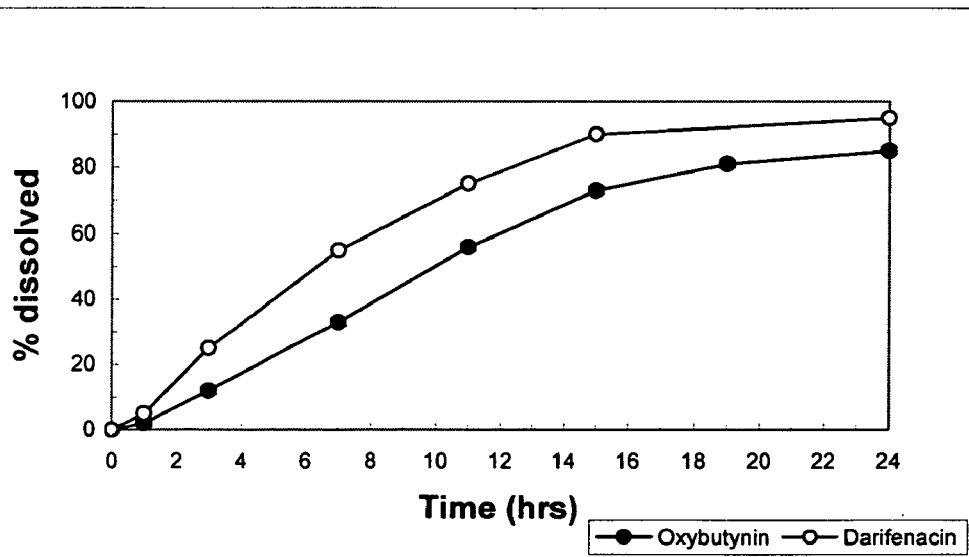

DUAL CONTROLLED RELEASE OSMOTIC DEVICE

CROSS-REFERENCE TO EARLIER FILED APPLICATION

This application is a divisional of and claims the priority of U.S. application Ser. No. 09/992,488 filed Nov. 6, 2001, now abandoned, the entire disclosure of which is hereby incorporated by reference.

FIELD OF THE INVENTION

This invention pertains to pharmaceutical compositions containing oxybutynin and at least one other drug for the treatment of incontinence. More particularly, it pertains to pharmaceutical compositions and dosage forms containing oxybutynin and darifenacin or oxybutynin and tolterodine and methods of using the same.

BACKGROUND OF THE INVENTION

Oxybutynin is useful for treating stress and urge urinary incontinence (over active bladder). DITROPAN™ tablets are commercially available tablets that provide a rapid release of oxybutynin in the stomach and upper intestinal tract. Rapid release tablets are typically administered at a rate of about 3-4 tablets per day to treat urinary incontinence. Rapid release tablets, however, typically have undesirable side effects associated with them due to the high plasma oxybutynin concentrations they provide. These tablets also have a short duration of action due to the short half-life ($t_{1/2} \approx 2$ hr) of oxybutynin in plasma.

In order to overcome these disadvantages, controlled release tablets of oxybutynin have been developed. In general, known controlled release tablets provide a sustained delivery of oxybutynin for a period of up to 8-30 hours after administration depending upon the formulation used. Sequential administration (2-3 times per day) of oxybutynin tablets having the same release profile is known.

A number of publications disclose controlled release formulations containing oxybutynin: a) U.S. Pat. No. 5,788,987 to Busetti et al.; b) International Publication No. WO 00/19997 to Alza Corp.; c) International Publication No. WO 96/12477 to Leiras OY; and d) Japanese Patents No. 2,646, 170 and No. 2,665,858 to Nippon Hoechst Marion Roussel Ltd. A number of scientific publications disclose extended and controlled release formulations containing oxybutynin. In addition, Alza Corporation currently markets DITROPAN XL™, which is a controlled release tablet formulation containing oxybutynin. None of these publications disclose a combination formulation or pharmaceutical composition containing oxybutynin and another drug.

U.S. Pat. No. 5,399,359 to Baichwal, the entire disclose of which is hereby incorporated by reference, discloses many different controlled release tablet formulations that provide a controlled release of oxybutynin for periods of up to 8, 12, 16, 18, 24 or 30 hours. This patent does not disclose the combined administration of oxybutynin and another drug used to treat incontinence.

U.S. Pat. No. 5,912,268, No. 5,840,754 and No. 5,674,895 to Guittard, the entire disclosures of which are hereby incorporated by reference, disclose osmotic device formulations that deliver oxybutynin at a controlled rate for a period of about 24 hours. This patent does not disclose the combined administration of oxybutynin and another drug used to treat incontinence.

Appell et al. ("Clinical Evaluation of a Sustained Release Form of Oxybutynin, *Urodynamics Society Symposium Abstracts* (1990), pg. 228), the entire disclosure of which is hereby incorporated by reference, discloses a controlled release tablet DITROPAN™ SR that provides a controlled delivery of oxybutynin for about 8-12 hours. This publication does not disclose the combined administration of oxybutynin and another drug used to treat incontinence.

Sirkiä et al. ("Use of hydrophilic polymers to control drug release from press-coated oxybutynin hydrochloride tablets", *S.T.P. Pharmacia Sci*. (1993), 3(6), pg. 453-458), the entire disclosure of which is hereby incorporated by reference, discloses a controlled release tablet formulation that provides a controlled delivery of oxybutynin for about 8-12 hours. This publication does not disclose the combined administration of oxybutynin and another drug used to treat incontinence.

Japanese Patent Applications Serial No. 9,388 and No. 163,901 to Enomoto et al., the entire disclosures of which are hereby incorporated by reference, disclose controlled release tablet formulations that deliver oxybutynin at a controlled rate for a period of about 12 hours for once or twice-a-day administration. These patents do not disclose the combined administration of oxybutynin and another drug used to treat incontinence.

A number of scientific publications disclose the results of tests on the therapeutic, pharmacological and/or pharmacodynamic properties of formulations containing darifenacin ((S)-2-[1-[2-(2,3-dihydrobenzofuran-5-yl)ethyl]-3-pyrrolidinyl]-2,2-diphenyl-acetamide). The darifenacin formulations described in these publication include only i.v., i.p., and immediate release formulations. None of these references, however, disclose the combined administration of darifenacin and oxybutynin.

International Publication No. WO 97/09980 and U.S. Pat. No. 6,106,864 to Dolan et al. of Pfizer, Inc. discloses a controlled release formulation comprising darifenacin, wherein at least 10% of the darifenacin is delivered to the lower gastrointestinal tract. Dolan et al. disclose that the controlled release formulation can be any of a number of different formulations, including osmotic devices, as long as it provides the specified release profile. Dolan et al., however, do not disclose or suggest the coadministration of oxybutynin with darifenacin.

Dmochowski et al. (*Urology* (2000), 56(6), Suppl. A, pp. 41-49) disclose a number of different therapeutic agents for the treatment of incontinence. Dmochowski et al., however, do not disclose or suggest the coadministration of oxybutynin with darifenacin.

International Publication No. WO 97/18814 to Pfizer Research and Development Company discloses a number of controlled release formulations. One example in the disclosure includes a controlled release tablet comprising darifenacin. This publication also does not disclose or suggest the coadministration of oxybutynin with darifenacin.

A number of scientific publications disclose the results of clinical tests comparing the therapeutic, pharmacological, and/or pharmacodynamic properties of formulations containing tolterodine ((R)-N,N-diisopropyl-3-(2-hydroxy-5-methylphenyl)-3-phenylpropylamine). The formulations include controlled, immediate or rapid release formulations. None of these references, however, disclose the combined administration of tolterodine and oxybutynin.

International Publication No. WO 00/12069 to Pharmacia Upjohn AB discloses controlled release formulations containing tolterodine. This publication, however, does not disclose a combination formulation containing tolterodine and oxybutynin. In addition, Pharmacia Upjohn currently markets DETROL LA™, which is an extended release capsule formulation containing tolterodine.

Side effects in drug therapies for the treatment of incontinence continue to be a problem. Practitioners are in search of therapies having an improved toxicity profile, enhanced therapeutic efficacy or reduced total drug dose requirement.

Osmotic devices and other tablet formulations are known for their ability to provide a controlled release of a wide range of drugs. Such osmotic devices and other tablet formulations are disclosed in U.S. Pat. No. 4,014,334 to Theeuwes et al., U.S. Pat. No. 4,576,604 to Guittard et al., Argentina Patent No. 234,493, U.S. Pat. No. 4,673,405 to Guittard et al., U.S. Pat. No. 5,558,879 to Chen et al., U.S. Pat. No. 4,810,502 to Ayer et al., U.S. Pat. No. 4,801,461 to Hamel et al., U.S. Pat. No. 5,681,584 to Savastano et al., U.S. Pat. No. 3,845,770 and Argentina Patent No. 199,301, the entire disclosures of which are hereby incorporated by reference.

Osmotic devices have demonstrated utility in delivering beneficial active agents, such as medicines, nutrients, food, pesticides, herbicides, germicides, algaecides, chemical reagents, and others, to an environment of use in a controlled manner over prolonged periods of time. Known devices include tablets, pills, and capsules.

Advancements in the art have focused on developing osmotic devices with improved semipermeable or porous membranes, various coatings surrounding the core and/or the semipermeable membrane, layered osmotically effective agents in the core of the device, specific release profiles for specific active substances, and specific membrane or core compositions.

U.S. Pat. Nos. 4,931,285, 5,006,346 and 5,160,743 to Edgren et al., U.S. Pat. Nos. 5,160,744, 5,190,765 and No. 5,252,338 to Jao et al., U.S. Pat. Nos. 4,612,008, 4,765,989 and No. 5,082,668 to Wong et al., U.S. Pat. No. 4,327,725 to Cortese et al., U.S. Pat. No. 5,208,037 to Wright et al., U.S. Pat. No. 4,904,474 to Theeuwes et al. and U.S. Pat. No. 4,627,971 to Ayer disclose osmotic devices comprising a bi-layered core surrounded by a semipermeable membrane having at least one hole (or passageway). The bi-layered core, however, comprises a first push-layer containing no drug and a second layer containing drug. The hole(s) can be placed anywhere along the semipermeable membrane. These patents do not disclose a core having two different drug-containing layers, each providing a controlled release of drug through a respective hole in the semipermeable membrane.

U.S. Pat. No. 5,543,155 to Fekete et al. discloses an osmotic device comprising a bi-layered core surrounded by a semipermeable membrane having two holes (or passageways). The bi-layered core, however, comprises a first push-layer containing no drug and a second layer containing drug. The hole(s) can be placed anywhere along the semipermeable membrane. This patent does not disclose a core having two different drug-containing layers, each providing a controlled release of drug through a respective hole in the semipermeable membrane.

U.S. Pat. No. 4,662,880 to Hamel et al., U.S. Pat. Nos. 4,723,957, 4,867,969 and 4,971,790 to Magruder et al. disclose osmotic devices comprising a single-layered core surrounded by a semipermeable membrane having two oppositely placed holes. A drug-containing coat further surrounds the semipermeable membrane. These patents do not disclose a core having two different drug-containing layers, each providing a controlled release of drug through a respective hole in the semipermeable membrane.

U.S. Pat. No. 4,624,847 to Ayer et al. discloses an osmotic device comprising a semipermeable membrane surrounding a compartment that houses a drug-containing polymer that increases in size and releases drug. The semipermeable membrane has two oppositely placed holes for releasing drug. These patents do not disclose a core having two different drug-containing layers, each providing a controlled release of drug through a respective hole in the semipermeable membrane.

U.S. Pat. No. 4,915,954 to Ayer et al. and U.S. Pat. No. 4,814,181 to Jordan et al. disclose an osmotic device having a bi-layered core surrounded by a semipermeable membrane. The first layer comprises a first drug that is released from the core rapidly over a period of 2 min to 2 hr. The second layer comprises a second drug that is released from the core at a controlled rate over a long period of time. The layers of the core are in intimate contact and are not separated by another layer, lamina or membrane. The semipermeable membrane can have two holes, one hole adjacent each of the two layers of the core such that each layer releases drug through its own respective hole. The Ayer et al. and Jordan et al. patents do not disclose an osmotic device having a bi-layered core, wherein the layers are in contact with each other and in laminar arrangement with respect to one another and wherein each layer provides a prolonged and controlled release of an active agent.

U.S. Pat. No. 4,455,143 to Theeuwes et al. discloses an osmotic device having two compartments defined by a surrounding semipermeable membrane and a partition between the compartments. The semipermeable membrane has two oppositely placed holes, one for each compartment. Each compartment contains a drug that is delivered at a controlled rate through a respective hole in the surrounding membrane. The partition is require and retains its integrity during operation of the osmotic device.

U.S. Pat. No. 5,866,164 to Kuczynski et al. of Alza Corporation discloses an osmotic device having a bi-layered core surrounded by a semipermeable membrane. There is no partition between the layers. The core includes a drug-containing layer and a push-layer; and passageways in the surrounding semipermeable membrane only communicate the drug-containing layer, and not the push-layer, to the exterior of the device. This osmotic device was specifically designed to release only the drug in the drug-containing layer and retain the drug in the push-layer.

While the prior art discloses a wide variety of osmotic devices, none of the prior art discloses an osmotic device that provides a controlled delivery of at least two different active agents, wherein: a) the core of the osmotic device is bi-layered and comprises a first pharmaceutical composition in laminar arrangement with a second pharmaceutical composition; b) the pharmaceutical compositions are in contact with one another; and c) drug is released from each layer through a passageway in a surrounding membrane (coat).

None of the prior art discloses a method of treating incontinence by coadministering oxybutynin with another drug, such as darifenacin or tolterodine. Likewise, none of the references disclose a pharmaceutical composition, or dosage form, comprising a combination of darifenacin and oxybutynin or of tolterodine and oxybutynin.

None of the prior art discloses an osmotic device comprising a dual layered core, wherein each layer of the core provides a controlled release of its respective drug and wherein the layers are in intimate contact, i.e., the layers are not separated by a partition, and wherein neither layer is required to be a push-layer, per se.

SUMMARY OF THE INVENTION

The present invention provides a pharmaceutical composition for the treatment of incontinence. The pharmaceutical composition can be administered to a subject by any conventional means. The pharmaceutical composition comprises:

oxybutynin present in a sub-therapeutic or therapeutic amount; and a second drug for treating incontinence present in a sub-therapeutic or therapeutic amount; wherein the oxybutynin and second drug together provide a therapeutic benefit in the treatment of incontinence.

The pharmaceutical composition of the invention can also comprise oxybutynin, a second drug for treating incontinence, and at least one pharmaceutical excipient.

Specific embodiments of the invention include those wherein: a) the second drug is darifenacin or tolterodine; 2) at least one of the oxybutynin and the second drug is present in a therapeutic amount; 3) the oxybutynin and the second drug are each present in a therapeutically effective amount; 4) at least one of the oxybutynin and the second drug is present in a sub-therapeutically effective amount; 5) the pharmaceutical composition is included in a dosage form; 6) the oxybutynin and second drug together provide a synergistic therapeutic effect; 7) the oxybutynin and second drug together provide an additive therapeutic effect; 8) the pharmaceutical composition, when administered to a subject, has an improved toxicity (side effect) profile over oxybutynin or the second drug when either agent is administered alone in a therapeutic amount to the same subject; 9) the pharmaceutical composition is a manufactured batch; 10) the pharmaceutical composition is a homogeneous or heterogeneous mixture; and/or 11) the weight ratio of oxybutynin to second drug is in the range of about 1:0.1 to 1:10.6 or 1:0.1 to 1:20.

Other specific embodiments of the invention include those wherein: 1) oxybutynin and the second drug are present in different compositions; 2) the pharmaceutical composition is adapted for oral, buccal, ocular, otic, dermal, rectal, vaginal, parenteral, sublingual, nasal, or pulmonary delivery; 3) the molar ratio of oxybutynin to second drug is in the range of about 1:0.08 to 1:8.2 or 1:0.05 to 1:15; 4) the pharmaceutical composition is a solid dosage form that independently provides a controlled, delayed, sustained, immediate, timed, slow, extended, targeted, pulsatile or rapid release of each of oxybutynin and the second drug; 5) the pharmaceutical composition provides therapeutically effective plasma levels of oxybutynin and the second drug for a period of at least 12 hours after administration; 6) the pharmaceutical composition comprises two different drug-containing compositions that are in admixture, separate, or in contact with one another; 7) the pharmaceutical composition comprises two different drug-containing compositions that are stacked or wherein one composition surrounds the other; 8) oxybutynin and the second drug have the same release profile; and/or 9) oxybutynin and the second drug have different release profiles.

Yet another aspect of the invention provides a rapid release dosage form comprising oxybutynin and a second drug for treating incontinence, wherein each drug is released rapidly and the dosage form provides therapeutically effective levels of each drug for a period of at least 3-8 hours. The plasma levels of drug are either independent of or dependent upon one another.

The pharmaceutical composition of the invention can be included in any dosage form suitable for the administration of drugs to a subject for the treatment of incontinence. Suitable dosage forms for administration of the drug combination to a subject are selected from the group consisting of a tablet, osmotic device, capsule, tape, suspension, liquid, implant, gel, inhaler, paste, pill, cream, ointment, troche, lozenge, granulation, particulate solid, powder, extruded solid, suppository, stick, mini-pump (such as the ALZET™ osmotic pump which is a miniature implantable pump). The dosage form can be coated or uncoated. The dosage form can be tailored for oral, ocular, nasal, vaginal, glandular, gastrointestinal tract, rectal, cervical, intrauterine, arterial, venous, otic, ophthalmic, sublingual, dermal, epidermal, subdermal, implant, buccal, bioadhesive, or mucosal administration.

The dosage form containing the drug combination can provide a release of each drug that is independently rapid, immediate, delayed, timed, targeted, sustained, controlled, slow, pulsatile or extended. In other words, the release profile for the oxybutynin can be independent of or dependent upon the release profile for the second drug. For example, the oxybutynin may be released in a controlled manner and the second drug may be released in a delayed and rapid manner. Specific embodiments of the invention include those wherein the dosage form provides a controlled release of both oxybutynin and the second drug.

Oxybutynin and the second drug can be included in a dosage form and pharmaceutical composition as: 1) a homogeneous mixture; or 2) a heterogeneous mixture. For example, the oxybutynin can be included in a first granulated composition and the second drug can be included in a second granulated composition and a heterogeneous mixture of both compositions can be used to fill capsules. The drugs can also be separate in the dosage form, for example as separate parts of the same dosage form. Accordingly, oxybutynin and the second drug can be located in the same composition or in different compositions in the same dosage form. In Examples 1, 2, 7, 8 and 12, the oxybutynin and the second drug are located in different compositions in the same dosage form. In examples 3, 4, 5, 6, 9, 10 and 11, the oxybutynin and the second drug are located in the same composition.

The invention also provides a method of treating incontinence by administering to a subject oxybutynin and a second drug used in the treatment of incontinence. The oxybutynin and the second drug can be administered concurrently, sequentially, in an overlapping manner or in a spaced apart manner.

Specific embodiments of the invention include those wherein: 1) the oxybutynin and the second drug are administered in the same dosage form; and/or 2) the oxybutynin and the second drug are administered in separate dosage forms.

When the oxybutynin and the second drug for treating incontinence are provided in separate dosage forms, the invention provides a kit comprising at least one first dosage form comprising oxybutynin and at least one second dosage form comprising the second drug.

In one embodiment, the invention provides a dosage form comprising:

oxybutynin present in a sub-therapeutic or therapeutic amount; and a second drug for treating incontinence present in a sub-therapeutic or therapeutic amount; wherein the oxybutynin and second drug together provide a therapeutic benefit in the treatment of incontinence.

Specific embodiments of the invention include those wherein: 1) the dosage form provides a sustained delivery of oxybutynin and of the second drug for about one day or a period of about 18-26 hours, and preferably about 24 hours; 2) the dosage form begins to release oxybutynin and then begins to release the second drug; 3) the dosage form begins to release the second drug and then begins to release the oxybutynin; 4) the dosage form provides a therapeutic benefit sufficient for once-daily administration; and/or 5) the dosage form is an oral dosage form that delivers drug to the various regions of the intestinal tract including the buccal cavity, esophagus, stomach, duodenum, jejunum, small intestine, large intestine and/or rectum.

Target therapeutic levels of oxybutynin are in the range of about 1-12 ng, preferably 3-8 ng and more preferably 4-7 ng, of oxybutynin per ml of plasma. Target therapeutic levels for darifenacin are those levels that are sufficient to provide the desired therapeutic response in a subject. Target therapeutic levels for tolterodine are in the range of about 0.5 to 25 ng per ml of plasma.

The present invention also provides an osmotic device that provides a controlled release device of two or more different active agents. The core of the osmotic device is bi-layered such that the two layers are in intimate contact with each other. Each layer comprises a respective pharmaceutical composition that provides a controlled release of a respective active agent. The core is surrounded by a membrane having at least one or two preformed holes. At least one hole in the membrane contacts the first layer of the core, and at least one hole in the membrane contacts the second layer of the core. The first pharmaceutical composition provides a controlled release of a first active agent through its respective first preformed passageway(s) in the semipermeable membrane. The second pharmaceutical composition provides a controlled release of a second active agent through a respective second passageway(s) in the semipermeable membrane. Both layers deliver their respective active agent through osmotic pumping. The first and second passageways can be located anywhere on their respective portions of the semipermeable membrane; however, the first and second passageways can oppose one another.

One aspect of the invention provides a dual controlled release osmotic device comprising:

a core comprising a first layer and a second layer, wherein the layers are in laminar arrangement and in intimate contact with one another; and a semipermeable membrane surrounding the core, wherein the membrane comprises at least two preformed passageways, wherein at least one first passageway is in communication with the first layer and at least one second passageway is in communication with the second layer;

whereby the first layer provides a controlled release of a first active agent through the first passageway according to a first release profile and the second layer provides a controlled release of a different second active through the second passageway according to a second release profile.

Specific embodiments of the invention include those wherein: a) the release profile for the first active agent approximates the release profile of the second active agent; b) the release profile of the first active agent is different than the release profile of the second active agent; c) the first active agent is delivered to the upper to middle GI tract and the second active agent is delivered to the upper to lower GI tract of a mammal to which the dual osmotic device is delivered; d) the first and second active agents are delivered in a concurrent, sequential or overlapping manner; e) the first active agent is oxybutynin and the second active agent is a different drug used for the treatment of incontinence; f) the first active agent is delivered to the upper to middle GI tract and the second active agent is delivered to the middle to lower GI tract of a mammal to which the osmotic device is delivered; and/or g) neither of the first or second layers is a "push-layer".

Another aspect of the invention provides a dual controlled release osmotic device comprising:

a core comprising a first active agent-containing layer and a second active agent-containing layer; and a semipermeable membrane surrounding the core, wherein the membrane comprises at least one preformed passageway in communication with at least one of the first and second active agent-containing layers;

whereby the osmotic device provides a controlled release of the first active agent through the at least one preformed passageway according to a first release profile and the second layer provides a controlled release of the second active through the at least one preformed passageway according to a second release profile.

Specific embodiments of the invention include those wherein: 1) the layers are in stacked arrangement and in contact with one another; 2) the second active-agent containing layer surrounds the first active agent containing layer; 3) the osmotic device comprises at least one first preformed passageway in communication with the first active agent-containing layer and at least one second preformed passageway in communication with the second active agent-containing layer; 4) the membrane comprises at least one preformed passageway in communication with both the first and second active agent-containing layers; 5) the membrane comprises at least two preformed passageways and at least one of the two preformed passageways is plugged with a water soluble or water erodible material; 6) the membrane comprises at least two preformed passageways both of which are plugged with a water soluble or water erodible material, wherein the material plugging the first passageway may be the same as or different than the material plugging the second passageway; 7) the passageway(s) are plugged by the material comprising an external finish coat; 8) the osmotic device further comprises one or more coats interposed the semipermeable membrane and the core; 9) the osmotic device further comprises one or more coats external to the semipermeable membrane; 10) the osmotic device further comprises an external coat surrounding the membrane, and the membrane comprises at least a first preformed passageway and at least a second preformed passageway, wherein the first passageway has been formed after application of the external coat to the membrane, and the second passageway has been formed before application of the external coat to the membrane such that the second passageway is plugged by the external coat, and release of the second drug begins after release of the first drug has started 11) the osmotic device further comprises an external coat surrounding the membrane, and the membrane comprises at least a first preformed passageway and at least a second preformed passageway, wherein the first and second passageways have been formed before application of the external coat to the membrane; and the first and second passageways are plugged by the external coat; 12) the first and second active agents are the same; 13) the first and second active agents are different; and/or 14) the external coat comprises one or more active agents that are the same as or different than the first and second active agents.

Yet another aspect of the invention provides an osmotic device comprising:

a core comprising a first composition comprising a first drug and at least one pharmaceutical excipient, and a different second composition comprising a second drug and at least one pharmaceutical excipient, wherein the first and second compositions contact one another and are in stacked arrangement; and a membrane enveloping the core and having at least two passageways to permit release of the first and second drugs from the core when the osmotic device is exposed to an aqueous environment, wherein at least one first passageway is in communication with the first composition and at least one second passageway is in communication with the second composition.

Still another aspect of the invention provides an osmotic device comprising:

a core comprising a first composition comprising oxybutynin and at least one pharmaceutical excipient, and a different second composition comprising a second drug, selected from the group consisting of darifenacin and tolterodine, and at least one pharmaceutical excipient; and a semipermeable membrane enveloping the core and having at least two passageways to permit controlled release of oxybutynin and the second drug from the core when the osmotic device is exposed to an aqueous environment, wherein at least one passageway is in communication with the first composition and at least one passageway is in communication with the second composition.

Specific embodiments of the invention includes those wherein: 1) the osmotic device provides an oxybutynin release profile as described herein; 2) the osmotic device provides a second drug release profile as described herein; 3) the osmotic device provides an oxybutynin plasma concentration profile as described herein; and/or 4) the osmotic device provides a second drug plasma concentration profile as described herein.

Another aspect of the invention provides a coated dosage form comprising:

a core comprising oxybutynin, a second drug for treating incontinence and at least one pharmaceutical excipient, wherein the second drug is selected from the group consisting of darifenacin and tolterodine; and a wall enveloping the core.

Specific embodiments of the invention include those wherein: 1) the wall is microporous, permeable, semipermeable or impermeable; 2) the wall further comprises one or more preformed passageways to permit release of oxybutynin and the second drug when the dosage form is exposed to an aqueous environment; 3) the wall is a multi-layered wall comprising two or more laminas that are independently selected at each occurrence from inert and drug-containing; 4) the two or more laminas are independently selected at each occurrence from microporous, permeable, semipermeable and impermeable; and/or 5) the two or more laminas are independently selected at each occurrence from water soluble and water erodible.

A more specific aspect of the invention provides an osmotic device comprising:

a core comprising a first composition comprising oxybutynin and at least one pharmaceutical excipient, and a different second composition comprising a second drug, selected from the group consisting of darifenacin and tolterodine, and at least one pharmaceutical excipient, wherein the first and second compositions contact one another and are in stacked arrangement; and a semipermeable membrane enveloping the core and having at least two passageways to permit controlled release of oxybutynin and the second drug from the core when the osmotic device is exposed to an aqueous environment, wherein at least one passageway is in communication with the first composition and at least one passageway is in communication with the second composition;

wherein, when the osmotic device is exposed to an aqueous environment, oxybutynin is released according to a release profile as described herein.

Other specific embodiments include those wherein: 1) the osmotic device provides a single dose plasma level for darifenacin is sufficient to provide a desired therapeutic response in a subject; 2) the osmotic device provides a single dose plasma level for oxybutynin in the range of about 4-7 or 1-10 ng per ml of plasma; 3) the osmotic device provides a single dose plasma level for tolterodine in the range of about 0.5-25 ng per ml of plasma; or 4) the osmotic device comprises a finish coat exterior to the semipermeable membrane.

The invention also provides a therapeutic device for the delivery of pharmaceutically active agents, ranging in solubility from slightly soluble to very soluble drugs, in a controlled, continuous and approximately steady, preferably zero order, rate over a prolonged period of time. Depending upon the excipients used, among other things, the osmotic device can also deliver drugs according to first order, pseudo-first order, release profiles. In addition, the osmotic device may provide targeted delivery of a drug.

The device of the present invention is optionally provided with an external coating disposed on the outside of the osmotic device and comprising one or more active agents for immediate delivery to the environment of use. The external coating can contain a loading dose of an active agent in the core of the device.

Active agents useful in the delivery device include, for example, compounds such as biologically or pharmacologically active agents, medicines, nutrients, food products, insecticides, pesticides, herbicides, germicides, algaecides, fungicides, chemical reagents, growth regulating substances, parasiticides, sex sterilants, fertility promoters, biocides, rodenticides, disinfectants, anti-oxidants, plant growth promoters, preservatives, fermentation agents, fertility inhibitors, deodorants, micro-organism attenuators, catalysts, food supplements, cosmetics, vitamins, and other agents that benefit the environment of use.

The osmotic device of the invention may be used in biological environments, aquariums, industrial warehouses, laboratory facilities, hospitals, chemical reactions and other facilities.

Other features, advantages and embodiments of the invention will become apparent to those of ordinary skill in the art by the following description, accompanying examples and appended claims.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

FIG. 6 depicts an in vitro release profile for oxybutynin and tolterodine as they are released from the osmotic device of Example 1.

FIG. 7 depicts an in vitro release profile for oxybutynin and darifenacin as they are released from the osmotic device of Example 2.

DETAILED DESCRIPTION OF THE INVENTION

Figure 1:
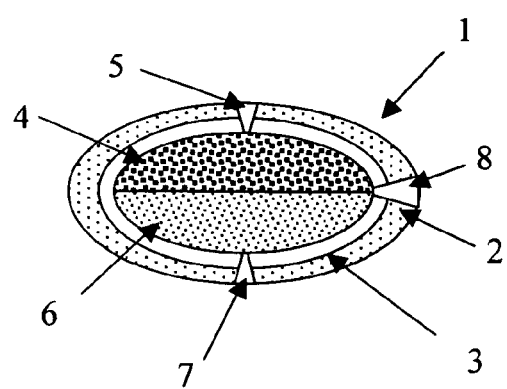
FIG. 1 depicts a sectional side view of a delivery device according to the present invention.

The present invention provides a pharmaceutical composition for treating incontinence. The pharmaceutical composition can be included in any dosage form. The pharmaceutical composition contains oxybutynin and another drug that is known to be useful in treating incontinence. Together, the oxybutynin and second drug provide an overall therapeutic benefit that is better than the overall therapeutic benefit provided by either agent when it is administered alone. The therapeutic benefit can include improved safety, reduced toxicity, improved efficacy, reduced number of overall side-effects, and/or reduced severity of one or more side-effects.

In one embodiment, oxybutynin and the second drug are released concurrently from a dosage form when the two drugs are included together in, for example, a tablet core, powder, capsule, bead, granule, liquid, paste, gel, cream, ointment, patch, implant or other similar dosage form capable of simultaneously delivering two or more drugs.

In another embodiment, oxybutynin and the second drug are released sequentially from a dosage form when the first drug is included in one part of a dosage form and the second drug is included in another part of the same dosage form, and release of the second drug begins shortly after, during or nearly at the end of completion of release of the first drug. Such dosage form would include, for example, those wherein the first drug is included in a core and the second drug is included in a coat surrounding the core, a bi-layered tablet with each drug being in a different part of the core, a dosage form providing a rapid release of the first drug and a controlled release of the second drug. Suitable dosage forms for this embodiment include, for example, a layered patch, layered or coated tablet or bead, layered or coated osmotic device, capsule containing a mixture of beads that provide different release profiles for the drugs, layered or coated implant, or an admixture of two compositions each containing a drug.

In yet another embodiment, oxybutynin and the second drug are released in spaced apart periods of time from a dosage form such that the first drug is released during a first period of time and the second drug is released during a later second period of time. Dosage forms suitable for this type of release are generally considered targeted, enteric or timed-release dosage forms. Suitable dosage forms for this embodiment include, for example, a layered patch, layered or coated tablet, layered or coated osmotic device, capsule containing a mixture of beads that provide different release profiles for the drugs, and layered or coated implant.

Each drug will be released independently from a solid dosage form according to a rapid, immediate, controlled, sustained, slow, timed, targeted, pseudo-first order, first order, pseudo-zero order, zero-order and/or delayed release profile. The particular release profiles for oxybutynin and the second drug in a particular dosage form will depend upon the specific combination of oxybutynin and second drug present and the excipients used to make the dosage form. For example, a dosage form might provide: 1) a controlled release of the first drug and a controlled release of the second drug; 2) a controlled release of the second drug and a rapid release of the first drug; 3) a controlled release of the first drug and a rapid release of the second drug; 4) a rapid release of the first drug and the second drug; 5) a rapid release of the first drug and a delayed but rapid release of the second drug; 6) a rapid release of the first drug and a timed but controlled release of the second drug; 7) a rapid release of the second drug and a delayed but rapid release of the first drug; 8) a rapid release of the second drug and timed but controlled release of the first drug; or 9) a controlled and delayed release of the first drug and a controlled but not substantially delayed release of the second drug.

Controlled release formulations containing the pharmaceutical composition of the invention can be made according to *Biorelated Polymers and Gels: Controlled Release and Applications in Biomedical Engineering* (ed. Teruo Okano; 1998); *Encyclopedia of Controlled Drug Delivery* (ed. Edith Mathiowitz; 1999); *Future Strategies for Drug Delivery with Particulate Systems* (ed. J. E. Diederichs; 1998); *Controlled Release Series* (ed. J. M. Anderson; 1987); *Controlled Drug Delivery Series* (Ed. S. D. Bruck; 1983); *Controlled Release of Drugs Series* (ed. M. Rosoff; 1989); *Controlled Release Technology: Pharmaceutical Applications* (ACS Symposium Series No. 348) (eds. P. I. Lee and W. R. Good; 1987); *Extended Release Dosage Forms* (ed. L. Krowczynski; 1987); *Handbook of Pharmaceutical Controlled Release Technology* (ed. D. L. Wise; 2000); *Intelligent Materials for Controlled Release* (ed. S. M. Dinh; 1999); *Multicomponent Transport in Polymer Systems for Controlled Release* (Polymer Science and Engineering Monograph Series) (ed. A. Polishchuk; 1997); *Pharmaceutical Technology: Controlled Drug Release* (ed. M. Rubenstein; 1987); *Polymers for Controlled Drug Delivery* (ed. P. J. Tarcha; 1991); *Tailored Polymeric Materials for Controlled Delivery Systems* (ACS Symposium Series No. 709) (ed. I. McCulloch; 1998); *Oral Colon-Specific Drug Delivery* (ed. D. R. Friend, 1992); and other publications known to those of ordinary skill in the art, the entire disclosures of which are hereby incorporated by reference. The dosage forms thereof can be amended as described herein to include oxybutynin and a second drug to treat incontinence.

Topical formulations for administering the pharmaceutical composition of the invention can be prepared as disclosed in *Electrically Assisted Transdermal and Topical Drug Delivery* (ed. A. K. Banga; 1998); *Topical Drug Bioavailability, Bioequivalence and Penetration* (ed. V. P. Shah; 1993); *Topical Drug Delivery Formulations* (ed. D. W. Osborne); *Transdermal and Topical Drug Delivery Systems* (ed. T. K. Ghosh; 1997); and other publications known to those of ordinary skill in the art, the entire disclosures of which are hereby incorporated by reference. The dosage forms thereof can be amended as described herein to include oxybutynin and a second drug to treat incontinence.

The pharmaceutical composition of the invention can also be administered in other dosage forms such as those disclosed in Handbook on Injectible Drugs 3rd Ed. (Trissel, 1983); Wang, et al., "Review of Excipients and pH's for Parenteral Products Used in the United States", *Journal of the Parenteral Drug Association* 14(6):452 (1980) and Hard Capsules Development and Technology (The Pharmaceutical Press, 1987), the disclosures of which are hereby incorporated by reference. The dosage forms thereof can be amended as described herein to include oxybutynin and a second drug to treat incontinence.

Oxybutynin is commercially available as the free base or in its hydrochloride salt form from Abbott Laboratories Pharmaceutical Division (United States of America), Seloc AG (France), Sifa Ltd, (Ireland), Orgamol SA, Synkem Div. Plasto SA, Cedex (France), Gruppo Lepetit SA, Garessio (Italy) and Juzen Chemical Co. Ltd. The invention provides for the administration of oxybutynin in its free base, racemic, optically enriched, optically pure (R)- or (S)-, and/or pharmaceutically acceptable salt forms. The optically pure and optically enriched forms of oxybutynin are available from Sepracor (United States of America). The oxybutynin can also be included in a prodrug form or metabolite form (desethyloxybutynin). Unless otherwise specified, the term oxybutynin refers to all of the above-described forms of oxybutynin.

Oxybutynin is available in a rapid release tablet dosage form from Alza (Palo Alto, Calif.), Rosemont (Denver, Colo.), Sidmark Laboratories (NJ), Vintage Pharmaceuticals (Huntsville, Ala.), Laboratorios Phoenix (Argentina), and Leiras OY (Finland). Oxybutynin is typically completely released from these tablet dosage forms within about 0.1-3.0 hours after administration. These dosage forms can be modified according to the present invention to include a second drug for treating incontinence.

Oxybutynin is available in controlled release osmotic device tablet dosage forms called DITROPAN™ XL from Alza Corporation (Palo Alto, Calif.) and called DITROPAN™ UD from Osmodex (Buenos Aires, Argentina) and as a non-osmotic device tablet dosage form called CYSTRIN™ CR from Leiras OY (Finland). Oxybutynin is released from these tablet dosage forms at a controlled rate over a period of about 24 hours. Controlled release dosage forms of oxybutynin can also be manufactured according to the U.S. and foreign patents and patent applications incorporated herein by reference, and in particular according to U.S. Pat. Nos. 5,399, 359, 5,912,268, 5,840,754, and 5,674,895, Japanese Patent Applications Serial No. 9,388 and No. 163,901. Controlled release dosage forms containing oxybutynin can also be prepared according to Nilsson et al. (*Neurourol. Urodyn.* (1997), 16(6), pg. 533-42), International Publications No. WO 95/23, 593, and No. WO 96/12,477 and U.S. Pat. No. 5,368,861, the entire disclosures of which are hereby incorporated by reference. These dosage forms can be modified according to the present invention to include a second drug for treating incontinence. Controlled release dosage forms can also be manufactured according to the examples herein.

Useful drugs suitable for the treatment of incontinence include darifenacin, tolterodine, amitryptyline, atropine, propantheline, imipramine, terodiline, dicyclomine, flurbiprofen, nitroflurbiprofen (HCT-1026), hyoscyamine, trospium, duloxetine, resiniferatoxin, desmopressin, propiverine, midodrine, glycopyrrolate, KRP-197, and others known to those of ordinary skill in the art. Other drugs suitable for the treatment of incontinence also include the histamine and serotonin compounds as disclosed in U.S. Pat. No. 5,877,198; the 1,2-diamino derivatives of cyclobutene 3-4 diones of U.S. Pat. No. 5,506,252, eg., (R)-4-[3,4-dioxo-2-(1,2,2-trimethyl-propylamino)-cyclobut-1-enylamino]-3-ethyl-benzonitrile; the pyrrole derivatives of U.S. Pat. No. 6,172,102; the 4,5-diamino derivatives of (1H)-pyrazoles of U.S. Pat. No. 6,172, 222; the selective vasopressin V2 agonists of U.S. Pat. No. 6,194,407; the (+)-venlafaxine derivatives of U.S. Pat. No. 6,197,828; the enantiomerically enriched(R,R)-glycopyrrolate as disclosed in U.S. Pat. No 6,204,285; the enantiomerically enriched(R)-trihexyphenidyl as disclosed in U.S. Pat. No. 6,207,681; the substituted esters, amides and ketones having smooth muscle relaxing properties of U.S. Pat. No. 6,207,852; the tropone derivatives of U.S. Pat. No, 6,221,868; the $\alpha_{1L}$-adrenoceptor agonist compounds disclosed in U.S. Pat. No. 6,268,389, e.g., 2-(3-dimethylamino-2-methylphe-nylimino)-imidazolidine; 2-(6-bromo-3-dimethylamino-2-methylphenylimino)imidazolidine; 2-(5-amino-2-chloro-4-dimethylamino-2-methylphenylimino)imidazolidine; 2-(2-chloro-5-trifluoromethylphenylamino)imidazolidine, 2-(3-amino-2-methylphenylimino)-imidazolidine, 2-(6-chloro-3-dimethylamino-2-methylphenylimino)imidazolidine and tiamenidine; the tricyclic pyridine N-oxides of U.S. Pat. No. 6,235,900; the compounds 4-[(2-tert-butylamino-3,4-dioxo-cyclobut-1-enylamino)-methyl]-3-chloro-benzonitrile and 3-(2,3dichloro-6-methyl-benzylamino)-4-(1,1-dimethyl-propylamino)-cyclobut-3-ene-1,2-dione disclosed in PCT International Publication No. WO 98/11888; the analogs of glutamic acid and gamma-aminobutyric acid disclosed in PCT International Publication No. WO 00/61135; the 1-amino ethylindole derivatives disclosed in PCT International Publication No. WO 00/61554; the quinolinomorphinan derivatives disclosed in PCT International Publication No. WO 01/05795; the compounds 5-(2-ethyl-2Htetrazol-5-yl)-1,2,3,6-tetrahydropyridine, 5-(2-ethyl-2H-tetrazol-5-yl)-1-methyl-1,2,3,6-tetrahydropyridine as disclosed in PCT International Publication No. WO 01/13918; the compounds (+)-tramadol, O-demethyl-tramadol, (+)-O-demethyltramadol, O-desmethyl-N-mono-desmethyl-tramadol, (+)-O-des-methyl-N-mono-desmethyl-tramadol as disclosed in PCT International Publication No. WO 01/24783, and the quinolinoisoquinoline derivatives disclosed in PCT International Publication No. WO 01/40225. Still other suitable drugs for the treatment of incontinence are disclosed in PCT International Publications No. WO 98/09948, No. WO 99/52856, No. WO 00/02846, No. WO 01/02406, No. WO 01/27104, No. WO 01/36375, No. WO 01/36418, No. WO 01/47503, No. WO 01/600352. Additional suitable drugs for the treatment of incontinence are disclosed in U.S. Pat. Nos. 6,159, 998, 6,172,041, 6,194,447, 6,218,404, and 6,248,549, the entire disclosures of which are hereby incorporated by reference. These drugs may be included as the second drug in the present pharmaceutical composition. Preferred second drugs include darifenacin and tolterodine.

Darifenacin can be used for treating irritable bowel syndrome and urinary incontinence. Darifenacin can be made according to the procedure described by Pfizer (European Patent No. 388,054 (1990) or Graul et al (*J. Drugs Future* (1996), 21(11), 1105-1108). Darifenacin is available in the (R)-, (S)-, optically enriched and racemic form as well as the free-base or salt form. The darifenacin can also be included in a prodrug form or metabolite form. Unless otherwise specified, the term darifenacin refers to all of the above-described forms of darifenacin.

A targeted or enteric release dosage form containing darifenacin can be prepared according to Dolan et al. (U.S. Pat. No. 6,106,864). The dosage form of Dolan et al. can be modified according to the present invention to include oxybutynin.

Darifenacin is generally administered at a dose of 5-75 mg daily.

Tolterodine can be made according to the procedure described by KabiVitrum (European Patent No. 325,571 (1989)) or Andersson et al. (*J. O. C.* (1998), 63, 8067-8070). Tolterodine is available in the (R)-, (S)-, optically enriched and racemic form as well as the free-base or salt form. The tolterodine can also be included in a prodrug form or metabolite form (such as PNU-200577; (R)-N,N-diisopropyl-3-(2-hydroxy-5-hydroxymethylphenyl)-3-phenylpropylamine). Unless otherwise specified, the term tolterodine refers to all of the above-described forms of tolterodine.

Tolterodine is generally administered at a dose of 2 to 4 or 0.5 to 5 mg daily.

The pharmaceutical composition and dosage forms of the invention are used to treat urinary (stress or urge) incontinence, also referred to as over active bladder (OAB). Since some of the drugs herein possess bimodal activities, the pharmaceutical composition and dosage form of the invention can be used treat inflammatory bowel syndrome.

The oxybutynin and second drug can be formulated as its pharmaceutically acceptable salts. As used herein, "pharmaceutically acceptable salts" refer to derivatives of the disclosed compounds, wherein the therapeutic compound is modified by making acid or base salts thereof. Examples of pharmaceutically acceptable salts include, but are not limited to, mineral or organic acid salts of oxybutynin. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. For acidic compounds, the salt may include an amine-based (primary, secondary, tertiary or quaternary amine) counter ion, an alkali metal cation, or a metal cation. Lists of suitable salts are found in texts such as Remington's Pharmaceutical Sciences, 18$^{th}$ Ed. (Alfonso R. Gennaro, ed.; Mack Publishing Company, Easton, Pa., 1990); Remington: the Science and Practice of Pharmacy 19$^{th}$ Ed. (Lippincott, Williams & Wilkins, 1995); Handbook of Pharmaceutical Excipients, 3$^{rd}$ Ed. (Arthur H. Kibbe, ed.; Amer. Pharmaceutical Assoc., 1999); the Pharmaceutical Codex: Principles and Practice of Pharmaceutics 12$^{th}$ Ed. (Walter Lund ed.; Pharmaceutical Press, London, 1994); The United States Pharmacopeia: The National Formulary (United States Pharmacopeial Convention); and Goodman and Gilman's: the Pharmacological Basis of Therapeutics (Louis S. Goodman and Lee E. Limbird, eds.; McGraw Hill, 1992), the disclosures of which are hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The tablet dosage forms useful in the present invention include, by way of example and without limitation, pressed tablets, layered tablets, osmotic device tablets, coated tablets, uncoated tablets, enteric coated tablets, multiple compressed tablets, centered tablets (tablets containing another tablet inside), prolonged release tablets, slow release tablets, buccal and sublingual tablets, and molded tablets.

FIG. 1 depicts a controlled release dosage form (1) including a bi-layered core, wherein the first drug-containing layer (4) is in laminar (stacked) arrangement with respect to the second drug-containing layer (6). The core is enveloped by a wall (3) having at least two preformed passageways (5, 7). The passageway (5) is in communication with the first drug-containing layer (4), and the passageway (7) is in communication with the second drug-containing layer (6). The dosage form also includes an optional external coat (2). As depicted, the passageways (5,7) is made after the external coat (2) is placed onto the wall (3).

The wall (3) can be microporous, permeable, impermeable or semipermeable. By "microporous" is meant a membrane that permits release of the active agent in the core by diffusion through micropores or pores in a surrounding membrane. By "permeable" is meant that the wall permits passage of fluid and of ingredient(s). By "impermeable" is meant that the wall does not permit passage of any fluid or ingredient(s). By semipermeable membrane is meant a membrane that permits the influx of a liquid from the exterior of the delivery device to the interior of the delivery device, while at the same allowing release of the active agent in the core by osmotic pumping through the preformed passageway in the semipermeable membrane. The wall can maintain or lose its physical integrity during use. The permeability and physical stability of the wall depend upon the materials used to make the wall.

The external coat (2) is optional and can be inert, i.e., excluding any active agent, or can contain one or more active agents, e.g., a drug-containing coat. The external coat can maintain or lose its physical integrity during use, i.e., the coat can be water soluble or water erodible. The physical stability of the wall depends upon the materials used to make the wall. If the external coat contains an active agent, the release rate of the active agent can be rapid, immediate, controlled, delayed, slow, sustained, timed, or targeted. The external coat can also include a loading dose of oxybutynin and the second drug in the core of the dosage form.

The core releases oxybutynin and the second drug; however, the rate of release of each is determined by the composition of the layer in which each is found, the composition of the wall (3) and the composition of the optional external coat (2). For example, when the wall (3) is a semipermeable or impermeable wall, the dosage form will provide a controlled release of both oxybutynin and the second drug. When the wall (3) is permeable or microporous, the dosage form will provide a more rapid and less controlled release of both oxybutynin and the second drug. Generally, the release rate of oxybutynin and the second drug from the core increases as the permeability of the wall (3) increases.

Unlike other known osmotic devices, the layers of the core in the osmotic device (1) can be adjacent and in intimate contact with one another. Each layer (4,6) releases its drug at a controlled rate. Surprisingly, the osmotic device does not require a push-layer, i.e., a layer that absorbs water and expands, in order to release drug from each layer or from the opposing surfaces of the osmotic device. Also, the osmotic device unexpectedly does not require a partition between the layers (4,6) of the core in order to release drug from each layer or from the opposing surfaces of the osmotic device.

Exemplary formulations for the dosage form (1) are detailed in Examples 1 and 2, wherein the dosage form is an osmotic device and includes an inert water soluble or erodible external coat (2) that does not contain drug. The osmotic device of Example 1 includes two different compositions in the core, which is surrounded by a semipermeable membrane. The first composition comprises oxybutynin, whereas the second composition comprises tolterodine. When this osmotic device is placed in an aqueous environment, it provides a controlled release of oxybutynin and tolterodine.

The dosage form (1) can also include: a) the external coat (2) as a drug-containing coat that contains oxybutynin and a second drug in rapid or immediate release form; b) the wall (3) as a water soluble or erodible coat; and c) a core as a controlled, slow, sustained, or rapid release core that contains oxybutynin and a second drug. Although the core is depicted in each figure as a bi-layered core, the invention includes embodiments wherein the core is a homogeneous or heterogeneous mixture of the drugs and pharmaceutical excipients.

The passageway of the device (1) can be in communication with both layers of the core. The passageway (8) extends through the external coat (2) and the wall (3) and communicates the exterior of the device to both compositions (4, 6) in the core. By using this type of construction, the device can deliver both drugs simultaneously through a single passageway.

The relative amounts of oxybutynin and second drug released at a given time can be controlled by changing the location of the passageway(s) in the wall (3). For example, if the first (4) and second (6) compositions have the same release properties and the device includes the sole passageway (5) centered on the composition (4), the device (1) will release a major portion of the first composition (4) before it releases any of the composition (6). If the first (4) and second (6) compositions have the same release properties and the device includes the sole passageway (5) in communication with the composition (4) and proximal but not in direct communication with the composition (6), the device (1) will release only a minor portion of the first composition (4) by the time it begins to release the second composition (6).

The relative amounts of oxybutynin and second drug released at a given time can be controlled by using compositions possessing predetermined release profiles. For example, if each composition (4, 6) has its own passageway (5, 7, respectively) located as depicted in FIG. 1, the device will provide a faster release of the drug in composition (4) if the composition (4) possesses a twelve-hour controlled release profile and the composition (6) possesses a twenty four-hour controlled release profile.

Where the coat (2) includes one or more drugs, those drugs can be the same as or different than the drugs in the core of the device. Therefore, the device can be used to deliver two or more different drugs.

Where the composition (4) includes an enteric release polymer and the composition (6) does not, the device (1) can provide a delayed and controlled release of the drug in the composition (4) and a controlled but not substantially delayed release of the drug in the composition (6).

Figure 2:
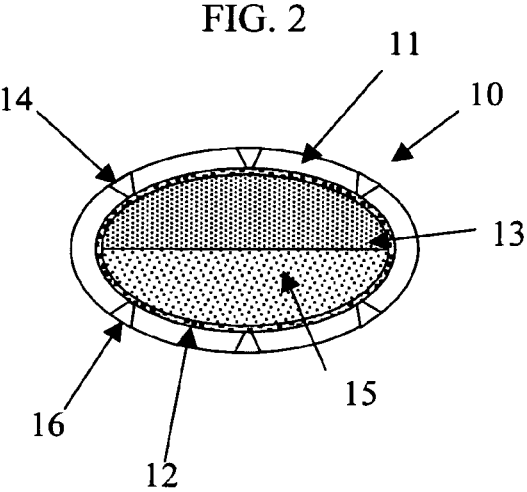
FIG. 2 depicts a sectional side view of an alternate delivery device according to the present invention.

FIG. 2 depicts an alternate embodiment of a controlled release dosage form according to the invention. The dosage form (10) includes a core comprising a first composition (13) in stacked arrangement with a second composition (15), wherein the core is enveloped by an internal coat (12) and then by a wall (11). The first composition (13) comprises oxybutynin and the second composition (15) comprises a second drug. The internal coat (12) can be an inert, release rate controlling, enteric, microporous, permeable, semipermeable, delayed release, water soluble, or water erodible coat. The wall (11) can be a microporous, impermeable, semipermeable or impermeable wall. The internal coat (12) and wall (11) have different compositions. The wall (11) includes plural passageways (14, 16). The passageways (14) permit release of oxybutynin from the core. The passageways (16) permit release of the second drug from the core. In one embodiment, the wall is a semipermeable wall, the internal coat is an inert water soluble or water erodible coat, and the dosage form provides a concurrent controlled release of oxybutynin and the second drug. Although not depicted in FIG. 2, the passageways (14, 16) can extend through the wall (11) and the internal coat (12).

When the internal coat (12) is a release rate-controlling coat, it will control the rate of release of the oxybutynin and the second drug. When the internal coat (12) is an enteric release coat, it will delay release of the oxybutynin and the second drug until the dosage form has reached the portion of the gastrointestinal tract downstream of the stomach, e.g, the ileum, duodenum, jejunum, intestines, colon and/or rectum. When the internal coat (12) is a microporous coat it will control release of the drugs from the core in a manner dependent upon the porosity of the coat, such that the rate of drug release increases as the porosity of the microporous coat increases.

As depicted, the passageways (14, 16) are not blocked by a water soluble or water erodible material, since no additional material is coated onto the wall (11) after the passageways are drilled.

Figure 3:
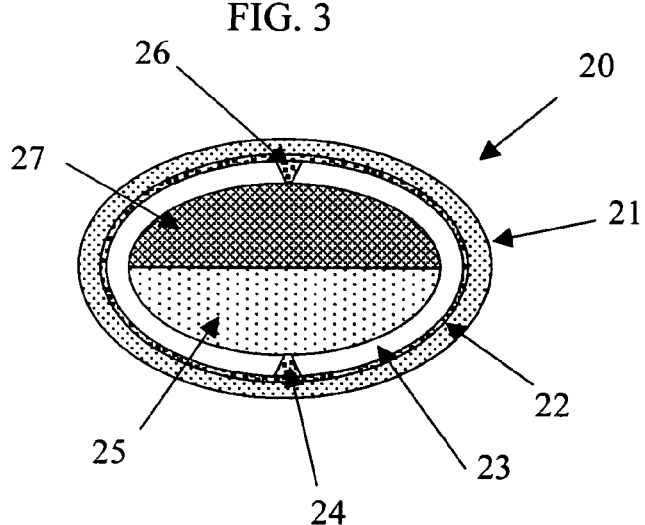
FIG. 3 depicts a sectional side view of a second alternate delivery device.

FIG. 3 depicts a controlled release dosage form (20) that includes a bi-layered core having first (27) and second (25) drug-containing layers. The core is surrounded by a wall (23), which is then surrounded by an internal coat (22) that does not contain drug. The external drug-containing or inert coat (21) surrounds the internal coat. The internal coat (22) is similar to and can include the same features of the internal coat (12) of the dosage form (10). The external coat (21) is similar to and can include the same features of the external coat (2) of the dosage form (1). The dosage form (20) provides a controlled release of oxybutynin through the passageway(s) (26) and a controlled release of the second drug through the passageway(s) (24).

The passageways (24,26) are plugged by the same material used to form the internal coat (22), since the internal coat is applied to the wall (23) after the passageways are drilled through the wall (23).

When the external coat (21) contains one or more drugs and the coat (22) is inert and water soluble or water erodible, the dosage form will provide a delayed release of both drugs from the core. The length of the delay may be as short as one minute or as long as several to many hours. For example, the delay may be 0.5-5.0 hours or 1.0-3.0 hours.

Figure 4:
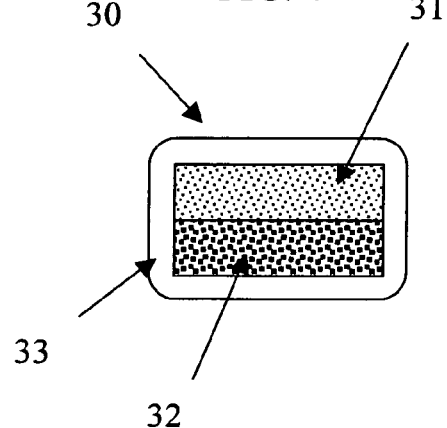
FIG. 4 depicts a sectional side view of a third alternate delivery device.

FIG. 4 depicts a bi-layered tablet (30) comprising a first composition (31) and a different second composition (32), wherein the tablet includes an optional coat (33). The coat (33) can be similar to and can include the same features of the external coat (2) or (21), the internal coat (12) or (22) or the wall (3), (11) or (23). Accordingly, the dosage form (30) can provide controlled, sustained, slow or extended release of oxybutynin and a second drug, optionally in a delayed or enteric release form.

The wall (33) can be a multi-layered wall comprising two or more lamina. At each occurrence, a lamina can be water soluble or water erodible and/or permeable, semipermeable, impermeable or microporous and/or inert or drug-containing. The wall can comprise one to six laminas.

Figure 5:
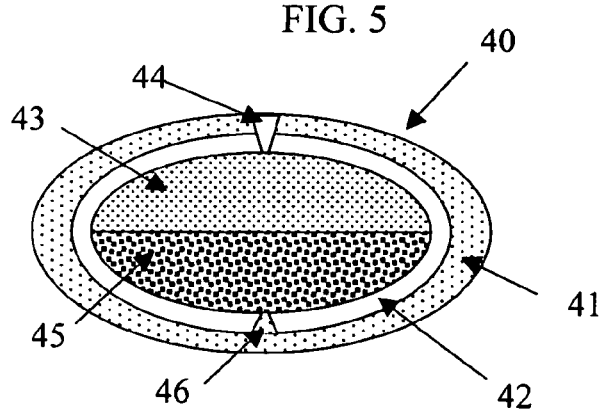
FIG. 5 depicts a sectional side view of a fourth alternate delivery device.

FIG. 5 depicts an osmotic device (40) comprising a bi-layered core surrounded by a semipermeable membrane (42), which is then surrounded by a drug-containing external coat (41). The osmotic device has two different types of preformed passageways. The passageway(s) (44), which communicates the drug-containing layer (43) of the core to the exterior of the device, is formed after the external coat is applied to the semipermeable membrane. The passageway(s) (46) is formed before the external coat is applied to the semipermeable membrane. Accordingly, the passageway(s) (46) is (are) plugged by the same material used to form the external coat (41). By virtue of its construction, this device will begin to release drug from the layer (43) before it begins to release drug from the layer (45). The delay period in the release of drug from the layer (45) is related to the amount of time it takes for the external coat (41) to dissolve or erode: the longer it takes to dissolve or erode, the longer the delay period for release of drug from the layer (45) through the passageway (46). The osmotic device (40), therefore, provides a controlled release of drug from the layer (43), wherein release begins shortly after exposure of the device to an environment of use, and a delayed and controlled release of drug from the layer (45), wherein release begins after release from the layer (43) has already begun.

FIG. 6 includes a dissolution profile for oxybutynin and tolterodine as they are released from the osmotic device of Example 1. The dissolution data is obtained in a paddle apparatus (USP type 2) operated at 100 rpm using distilled water at 37° C. as dissolution medium. The oxybutynin and tolterodine release profiles of the formulation of Example 1 are generally described as follows:

| | Oxybutynin Released | | | Tolterodine Released | | |
|---|---|---|---|---|---|---|
| | | Range (%) | | | Range (%) | |
| Time (hs) | Average (%) | Min | Max | Average (%) | Min | Max |
| 1 | 2 | 0 | 10 | 3 | 0 | 12 |
| 3 | 12 | 5 | 25 | 17 | 3 | 25 |
| 5 | 22 | 17 | 36 | 29 | 17 | 36 |
| 7 | 33 | 20 | 50 | 43 | 31 | 50 |
| 9 | — | — | — | 57 | 49 | 66 |
| 11 | 56 | 40 | 70 | 69 | 61 | 76 |
| 15 | 73 | 58 | 84 | 82 | 74 | 90 |
| 19 | 81 | 70 | 89 | — | — | — |
| 24 | 85 | 76 | 100 | 89 | 76 | 100 |

The dissolution profiles for oxybutynin and tolterodine approximate one another; however, the tolterodine has slightly faster rate of release. Although not shown in FIG. 6, the tolterdine can be made to achieve approximately complete dissolution at about 16 hours, and the oxybutynin can be made to achieve approximately complete dissolution at about 20 hours.

FIG. 7 includes a dissolution profile for oxybutynin and darifenacin as they are released from the osmotic device of Example 2. The dissolution data is obtained in a paddle apparatus (USP type 2) operated as indicated above. The oxybutynin and darifenacin release profiles of the formulation of Example 2 are generally described as follows:

| | Oxybutynin Released | | | Darifenacin Released | | |
|---|---|---|---|---|---|---|
| | Average | Range (%) | | Average | Range (%) | |
| Time (hrs) | (%) | Min | Max | (%) | Min | Max |
| 1 | 2 | 0 | 10 | 5 | 0 | 12 |
| 3 | 12 | 5 | 25 | 25 | 10 | 35 |
| 7 | 33 | 20 | 50 | 55 | 25 | 65 |
| 11 | 56 | 40 | 70 | 75 | 45 | 89 |
| 15 | 73 | 58 | 84 | 90 | 74 | 98 |
| 19 | 81 | 70 | 89 | — | — | — |
| 24 | 85 | 76 | 100 | 95 | 89 | 100 |

The darifenacin has a slightly faster rate of release. Although not shown in FIG. 7, the darifenacin can be made to achieve approximately complete dissolution at about 18 hours, and the oxybutynin can be made to achieve approximately complete dissolution at about 22 hours.

Figure 8:
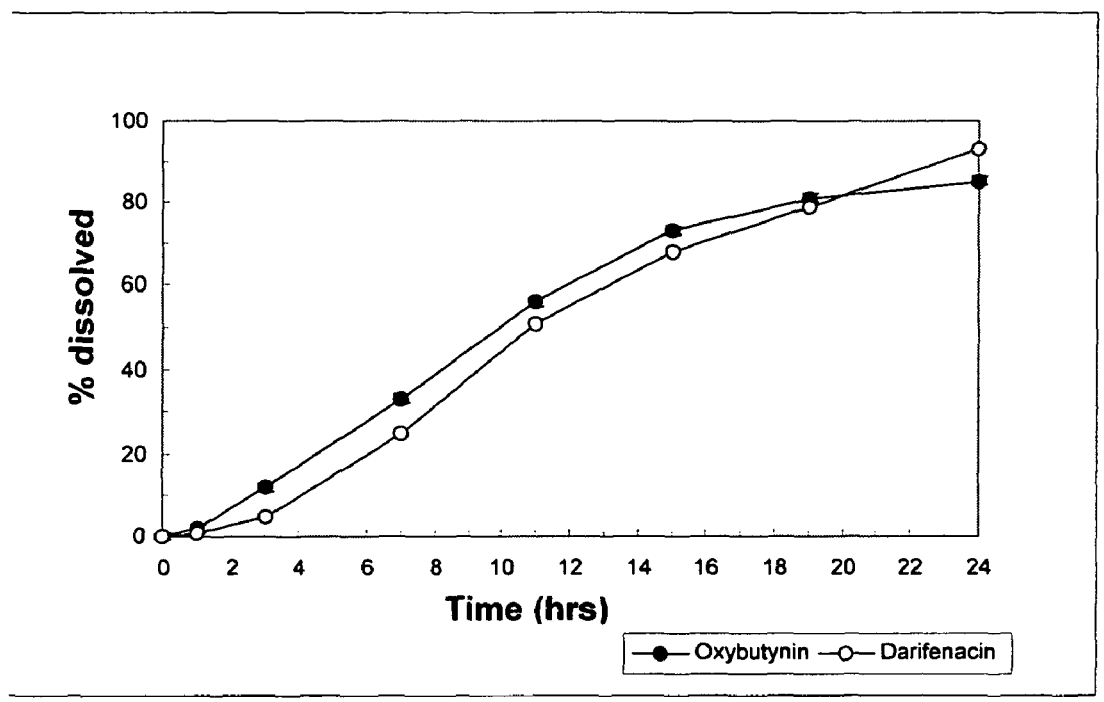
FIG. 8 depicts an in vitro release profile for oxybutynin and darifenacin as they are released from the osmotic device of Example 12.

FIG. 8 includes a dissolution profile for oxybutynin and darifenacin as they are released from the osmotic device of Example 12. The dissolution data is obtained in a paddle apparatus (USP type 2) operated as indicated above. The oxybutynin and darifenacin release profiles of the formulation of Example 12 are generally described as follows:

| | Oxybutynin Released | | | Darifenacin Released | | |
|---|---|---|---|---|---|---|
| | Average | Range (%) | | Average | Range (%) | |
| Time (hrs) | (%) | Min | Max | (%) | Min | Max |
| 1 | 2 | 0 | 10 | 1 | 0 | 5 |
| 3 | 12 | 5 | 25 | 5 | 0 | 15 |
| 7 | 33 | 20 | 50 | 25 | 10 | 45 |
| 11 | 56 | 40 | 70 | 51 | 29 | 74 |
| 15 | 73 | 58 | 84 | 68 | 52 | 84 |
| 19 | 81 | 70 | 89 | 79 | 60 | 89 |
| 24 | 85 | 76 | 100 | 93 | 80 | 100 |

The darifenacin and oxybutynin have approximately the same dissolution profile, but the oxybutynin has a slightly faster rate of release and slightly lower total amount released at 24 ours. Although not shown in FIG. 8, the darifenacin can be made to achieve approximately complete dissolution at about 24 hours, and the oxybutynin can be made to achieve approximately complete dissolution at about 20 hours.

A rapid release dosage form will contain about 0.01-5 mg, about 1-2.5 mg, or about 1-5 mg of oxybutynin, and about 2.5-50 mg of darifenacin, or about 0.5-4 mg or 2-4 mg of tolterodine. The rapid release dosage form will generally provide therapeutic levels of oxybutynin for a period of about 3-6 or about 2-8 hours after administration. It will also generally provide therapeutic levels of darifenacin for a period of several hours, or of tolterodine for a period of about 4 or about 2-6 hours after administration.

The rapid release tablets and short acting controlled release tablets, which are used as the first tablets of the invention, will provide therapeutically effective levels of oxybutynin generally for a period of less than 8 hours, preferably less than 6 hours. The short acting controlled release tablets, which are used as the second tablets of the invention, will provide therapeutically effective levels of oxybutynin generally for a period of not less than 16 hours and not more than 23 hours, preferably not less than 18 hours and not more than 22 hours.

When the dosage form is a controlled release dosage form, it will contain about 2.5-12.5 mg, about 5-12.5 mg, or about 5-10 mg of oxybutynin, and about 5-50 mg of darifenacin, or about 1-3 mg of tolterodine. The dosage form will provide therapeutic plasma concentration levels of oxybutynin for the period between about 0.5-24 hours or 1.5-24 hours after administration. The dosage form will generally provide therapeutic levels of darifenacin for a period of about 12-24 hours or 18-24. The dosage form will generally provide therapeutic levels of tolterodine for a period of about 12-24 hours or 18-24.

A specific embodiment of the dosage form includes a controlled release tablet that completely releases its oxybutynin charge within about 8 hours, or about 6 hours, after administration. Another embodiment of the tablet completes releasing its oxybutynin charge within about 23-24 hours after administration. A specific embodiment of the dosage form includes a controlled release tablet that completely releases its oxybutynin charge within about 8 hours, or about 6 hours, after administration, and releases its darifenacin charge in the colon.

A controlled release dosage form will provide effective amounts of oxybutynin for a period of not less than 18 hours and not more than 30 hours, or not less than 20 hours and not more than 28 hours, or not less than 22 hours and not more than 24 hours. The artisan of ordinary skill will understand that administration of a single unit dose period of time may be insufficient to maintain therapeutic plasma levels of oxybutynin for up to 24-30 hours and that multiple unit doses administered over an equal number of days may be required to maintain therapeutic plasma levels of oxybutynin for up to 24-30 hours.

Depending upon the particular combination of excipients used, a controlled release dosage form will independently provide an expected overall oxybutynin, darifenacin or tolterodine release profile that is pH-dependent or pH-independent; diffusion or dissolution controlled; pseudo-zero order, zero-order, pseudo-first order, first-order or second-order; or slow, delayed, timed or sustained release or otherwise controlled.

All of the formulations of the invention will provide sufficient levels of oxybutynin and darifenacin or tolterodine for at least a predetermined period of time to provide a desired therapeutic response.

The external coat can be applied to the surface of a tablet according to methods known to those of ordinary skill in the art. Such methods include, for example, applying solids in solution or suspension through the use of a sprayer that spreads them uniformly over the core or by employing compression or other suitable methods known to those of ordinary skill in the art. The external coat can comprise poly(vinyl pyrrolidone) (PVP) and poly(ethylene glycol) (PEG) and can further comprise materials such as, by way of example and without limitation, hydroxypropyl methylcellulose (HPMC), ethylcellulose (EC), hydroxyethylcellulose (HEC), sodium carboxymethylcellulose (CMC), dimethylaminoethyl methacrylate-methacrylic acid ester copolymer, ethyl acrylate-methyl methacrylate copolymer (GA-MMA), C-5 or 60 SH-50 (Shin-Etsu Chemical Corp.) and combinations thereof. The external coat can also comprise dissolution aids, stability modifiers, and bioabsorption enhancers When the external coat comprises a combination of materials, the relative amounts and ratios of those materials can be varied as desired. For example, when the external coat comprises PVP and PEG, the ratio of PVP:PEG will generally range from about 1-65% by weight of PVP: about 0.1-30% by weight of PEG based upon the weight of the external coat.

When oxybutynin and/or the second drug is present in the external coat, it is present in an amount ranging from about 0.1 to 99% by weight of the coat. This wide range provides great latitude in the design and application of the first tablet. Those of ordinary skill in the art will appreciate that the particular amount of drug employed will vary according to, among other things, the desired pharmacokinetic behavior in a mammal. For example, if the initial burst of drug release is intended to be small, then the external coat would include about 0.01 mg to about 0.5 mg of drug. If the initial burst of drug release is intended to be moderate, the external coat would include about 0.5 mg to about 5 mg of drug.

When a rapidly dissolving or eroding coat is used in the tablet formulations of the invention, the coat will generally comprise an inert and non-toxic material which is at least partially, and preferably substantially completely, soluble or erodible in an environment of use. The rapidly dissolving coat will be soluble in aqueous environments such as, for example, the buccal cavity and/or upper GI tract, e.g., the stomach, duodenum, jejunum or upper small intestines. Exemplary materials are disclosed in U.S. Pat. Nos. 4,576,604 and 4,673,405, and the text *Pharmaceutical Dosage Forms: Tablets Volume I, Second Edition*. (A. Lieberman. ed. 1989, Marcel Dekker, Inc.), the relevant disclosures of which are hereby incorporated by reference. In preferred embodiments, the rapidly dissolving coat will be soluble in saliva, gastric juices, or acidic fluids.

The long acting controlled release tablet formulations that provide a delayed and sustained release of oxybutynin and the second drug may include an enteric coat which is soluble or erodible in intestinal juices, substantially pH neutral or basic fluids but for the most part insoluble in gastric juices or acidic fluids. A wide variety of other polymeric materials are known to possess these various solubility properties. Such other polymeric materials include, by way of example and without limitation, cellulose acetate phthalate (CAP), cellulose acetate trimelletate (CAT), poly(vinyl acetate) phthalate (PVAP), hydroxypropyl methylcellulose phthalate (HP), poly (methacrylate ethyl acrylate) (1:1) copolymer (MA-EA), poly(methacrylate methyl methacrylate) (1:1) copolymer (MA-MMA), poly(methacrylate methyl methacrylate) (1:2) copolymer, Eudragit L-30-D™ (MA-EA, 1:1), Eudragit™ L-100-55™ (MA-EA, 1:1), hydroxypropyl methylcellulose acetate succinate (HPMCAS), Coateric™ (PVAP), Aquateric™ (CAP), AQUACOA™ (HPMCAS) and combinations thereof. The enteric coat can also comprise dissolution aids, stability modifiers, and bioabsorption enhancers.

When the enteric coat is intended to be dissolved, eroded or become detached from the core in the colon materials such as hydroxypropylcellulose, microcrystalline cellulose (MCC, Avicel™ from FMC Corp.), poly (ethylene-vinyl acetate) (60:40) copolymer (EVAC from Aldrich Chemical Co.), 2-hydroxyethylmethacrylate (HEMA), MMA, terpolymers of HEMA: MMA:MA synthesized in the presence of N,N'-bis(methacryloyloxyethyloxycarbonylamino)-azobenzene, azopolymers, enteric coated timed release system (Time Clock® from Pharmaceutical Profiles, Ltd., UK) and calcium pectinate can be used.

A polymeric material for use in the enteric coat involves materials that resist the action of gastric fluid avoiding permeation through the semipermeable wall while one or more of the materials in the core of the tablet are solubilized in the intestinal tract thereby allowing delivery of the drug in the core by osmotic pumping in an osmotic device to begin. A material that easily adapts to this kind of requirement is a poly(vinylpyrrolidone)-vinyl acetate copolymer, such as the material supplied by BASF under its Kollidon VA64 trademark, mixed with magnesium stearate and other similar excipients. The enteric coat can also comprise povidone, which is supplied by BASF under its Kollidon K 30 trademark, and hydroxypropyl methylcellulose, which is supplied by Dow under its Methocel E-15 trademark. The materials can be prepared in solutions of having different concentrations of polymer according to the desired solution viscosity. For example, a 10% P/V aqueous solution of Kollidon K 30 has a viscosity of about 5.5-8.5 cps at 20° C., and a 2% P/V aqueous solution of Methocel E-15 has a viscosity of about 13-18 cps at 20° C.

The enteric coat can comprise one or more materials that do not dissolve, disintegrate, or change their structural integrity in the stomach and during the period of time that the tablet resides in the stomach. Representative materials that keep their integrity in the stomach can comprise a member selected from the group consisting of (a) keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methylmethacrylate copolymer of 150,000 molecular weight, methacrylic acid-methyl methacrylate 50:50 copolymer of 135,000 molecular weight, methacrylic acid-methylmethacrylate-30:70-copolymer of 135,000 mol. wt., methacrylic acid-dimethylaminoethylmethacrylate-ethyl acrylate of 750,000 mol. wt., methacrylic acid-methyl methacrylate-ethyl acrylate of 1,000,000 mol. wt., and ethyl acrylate-methyl methacrylate-ethyl acrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

When the controlled release tablet is an osmotic device, the semipermeable membrane of the osmotic device is formed of a material that is substantially permeable to the passage of fluid from the environment of use to the core and substantially impermeable to the passage of active agent from the core. Many common materials known by those of ordinary skill in the art are suitable for this purpose. Exemplary materials are cellulose esters, cellulose ethers and cellulose esters-ethers. However, it has been found that a semipermeable membrane consisting essentially of cellulose acetate (CA) and poly(ethylene glycol) (PEG), in particular PEG 400, are preferred when used in combination with the other materials required in the present osmotic device. This particular combination of CA and PEG provides a semipermeable membrane that gives the osmotic device a well controlled release profile for the active agent in the core and that retains its chemical and physical integrity in the environment of use. The ratio of CA:PEG generally ranges from about 50-99% by weight of CA: about 50-1% by weight of PEG, and preferably about 95% by weight of CA: about 5% by weight of PEG. The ratio can be varied to alter permeability and ultimately the release profile of the osmotic device. Other preferred materials can include a selected member of the group of cellulose acylates such as cellulose acetate, cellulose diacetate, cellulose triacetate and combinations thereof. Many suitable polymers, include those disclosed in Argentine Patent No. 199,301 and other references cited herein, the disclosures of which are hereby incorporated by reference.

The osmotic device of the invention comprises at least one preformed passageway (pore, hole, or aperture) that communicates the exterior of the semipermeable wall with the core of the device. The preformed passageway can be formed according to any of the known methods of forming passageways in a membrane. Such methods include, for example, 1) drilling a hole through the semipermeable membrane with a bit or laser; 2) including a water soluble material within the composition that forms the semipermeable membrane such that a pore forms when the osmotic device is in an aqueous environment of use; 3) punching a hole through the semipermeable membrane; or 4) employing a tablet punch having a pin to punch a hole through the semipermeable lamina. The preformed passageway can pass through the semipermeable wall and one or more of any other lamina coated onto the semipermeable membrane or between the semipermeable membrane and the core. The passageway(s) can be shaped as desired. In some embodiments, the passageway is laser drilled and is shaped as an oval, ellipse, slot, slit, cross or circle. Micropores in a microporous membrane are distinguished from preformed passageways.

The depth of penetration of a preformed passageway can be tailored to provide specific drug release profiles, to control the extent to which release of a drug is delayed, and/or to control the order in which drugs are released. The order in which the process steps of forming a preformed passageway and applying a coating composition are conducted can be performed to provide specific drug release profiles, to control the extent to which release of a drug is delayed, and/or to control the order in which drugs are released.

Methods of forming passageways in membranes of osmotic devices are disclosed in U.S. Pat. No. 4,088,864 to Theeuwes et al., U.S. Pat. No. 4,016,880 to Theeuwes et al., U.S. Pat. No. 3,916,899 to Theeuwes et al., U.S. Pat. No. 4,285,987 to Ayer et al., U.S. Pat. No. 4,783,337 to Wong et al., U.S. Pat. No. 5,558,879 to Chen et al., U.S. Pat. No. 4,801,461 to Hamel et al., and U.S. Pat. No. 3,845,770 to Theeuwes et al., the disclosures of which are hereby incorporated by reference.

When the controlled release tablet is an osmotic device, osmotically effective solutes, osmotic agents or osmagents are added. These osmagents will aid in either the suspension or dissolution of oxybutynin and the second drug in the core. Exemplary osmagents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art. Osmagents can also be incorporated to the core of the osmotic device to control the release of oxybutynin therefrom.

The tablets of the invention can also comprise adsorbents, antioxidants, buffering agents, colorants, flavorants, sweetening agents, tablet antiadherents, tablet binders, tablet and capsule diluents, tablet direct compression excipients, tablet disintegrants, tablet glidants, tablet lubricants, tablet or capsule opaquants and/or tablet polishing agents.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent which inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dehydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "tablet antiadherents" is intended to mean agents which prevent the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "tablet binders" is intended to mean substances used to cause adhesion of powder particles in table granulations. Such compounds include, by way of example and without limitation, acacia, alginic acid, carboxymethylcellulose sodium, poly(vinylpyrrolidone), compressible sugar (e.g., NuTab), ethylcellulose, gelatin, liquid glucose, methylcellulose, povidone and pregelatinized starch and other materials known to one of ordinary skill in the art.

When needed, binders may also be included in the tablets. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, gelatin, cellulosics in nonaqueous solvents, combinations thereof and the like. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "tablet and capsule diluent" or "fillers" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "tablet direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "tablet glidant" is intended to mean agents used in tablet and capsule formulations to promote flowability of the granulation. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "tablet/capsule opaquant" is intended to mean a compound used to render a capsule or a tablet coating opaque. May be used alone or in combination with a colorant. Such compounds include, by way of example and without limitation, titanium dioxide and other materials known to one of ordinary skill in the art.

As used herein, the term "tablet polishing agent" is intended to mean a compound used to impart an attractive sheen to coated tablets. Such compounds include, by way of example and without limitation, carnauba wax, and white wax and other materials known to one of ordinary skill in the art.

As used herein, the term "tablet disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose (e.g., Avicel), carboxymethylcellulose calcium, cellulose polyacrilin potassium (e.g., Amberlite), alginates, sodium starch glycolate, gums such as agar, guar, locust bean, karaya, pectin, tragacanth and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carminic acid, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors that have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

The present formulations can also employ one or more commonly known surface active agents or cosolvents that improve wetting or disintegration of the tablet core or layers.

Plasticizers can also be included in the formulations to modify the properties and characteristics of the polymers used in the coats or core of the tablets. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

The formulations of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly (oxypropylene) copolymers; and amphoteric detergents, for example, alkyl β-aminopropionates and 2-alkylimidazoline quaternary ammonium salts; and mixtures thereof.

Various other components, not otherwise listed above, can be added to the present formulation for optimization of a desired active agent release profile including, by way of example and without limitation, glycerylmonostearate, nylon, cellulose acetate butyrate, d, 1-poly(lactic acid), 1,6-hexanediamine, diethylenetriamine, starches, derivatized starches, acetylated monoglycerides, gelatin coacervates, poly(styrene-maleic acid) copolymer, glycowax, castor wax, stearyl alcohol, glycerol palmitostearate, poly(ethylene), poly(vinyl acetate), poly(vinyl chloride), 1,3-butylene-glycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

The term "unit dose" is used herein to mean an amount of the pharmaceutical composition that is included in one or more dosage forms that together provide a therapeutically effective amount of oxybutynin and the second drug. Depending upon the specific combination and amounts of oxybutynin and second drug included within the dosage form, an improved, additive or synergistic therapeutic effect will be observed. Accordingly, a unit dose may include therapeutic or sub-therapeutic amounts of oxybutynin and the drug. An improved therapeutic effect is one wherein the second drug enhances the therapeutic benefit provided by oxybutynin alone. An additive therapeutic effect is one wherein each of oxybutynin and second drug possesses therapeutic properties, and the combination of the two drugs provides an overall therapeutic effect that approximates the sum of their individual therapeutic effects. A synergistic therapeutic effect is one wherein each of oxybutynin and second drug possesses therapeutic properties, and the combination of the two drugs provides an overall therapeutic effect that is greater than the sum of their individual therapeutic effects. In each embodiment of the invention, a particular combination of drugs will provide at least an improved therapeutic effect as compared to the individual drugs.

By the term "effective amount", it is understood that, with respect to, for example, pharmaceuticals, a therapeutically or sub-therapeutically effective amount is contemplated. A therapeutically effective amount is the amount or quantity of drug that is sufficient to elicit the required or desired therapeutic response, or in other words, the amount that is sufficient to elicit an appreciable biological response when administered to a patient. A sub-therapeutically effective amount is an amount that is less than the therapeutically effective amount when the dosage form of the invention is administered to a subject. The pharmaceutical composition and dosage form of the invention can contain therapeutically effective or sub-therapeutically effective amounts of oxybutynin and the second drug.

For nasal administration, the pharmaceutical composition may be included in a paste, cream, spray, powder, nebulizer, aerosol or ointment containing the appropriate solvents (such as water, aqueous, nonaqueous, polar, apolar, hydrophobic, hydrophilic and/or combinations thereof) and optionally other compounds (stabilizers, perfumes, antimicrobial agents, antioxidants, pH modifiers, surfactants and/or bioavailability modifiers). It is contemplated that bioavailability enhancers such as alcohols or other compounds that enhance the penetration of the therapeutic compound from the pharmaceutical formulation into the nasal mucosa may be needed to prepare suitable formulations for nasal administration.

For oral, buccal, and sublingual administration, the pharmaceutical composition may be in the form of a caplet, tablet, chewable tablet, suspension, agglomerate, granulate, lozenge, troche, or powder.

For rectal administration, the pharmaceutical composition can be included in a suppository, ointment, enema, tablet or cream for release of a therapeutic compound into the intestines, sigmoid flexure and/or rectum.

Tablets can differ in size, shape, color and amount of oxybutynin and the second drug. The tablets of the invention can assume any shape or form known in the art of pharmaceutical sciences. The device of the invention can be a pill, sphere, tablet, bar, plate, granule, agglomerate, paraboloid of revolution, ellipsoid of revolution or other shape known to those of ordinary skill in the art. The tablets can also include surface markings, cuttings, grooves, letters and/or numerals for the purposes of decoration, identification and/or other purposes.

The tablets of the invention can be prepared according to the methods disclosed herein or those well known in the art, more specifically according to the methods disclosed in the disclosure incorporated herein by reference. For example, according to one manufacturing technique, oxybutynin, the second drug and excipients that comprise the core are mixed in solid, semisolid or gelatinous form, then moistened and sieved through a specified screen to obtain uncoated cores. The uncoated cores are then dried in a dryer and compressed, for example, by punching.

If coated tablets are desired, the compressed and uncoated cores are then covered with a solution of suitable materials to provide the desired drug release profile. For example, if the tablet is to be an osmotic device, then the tablet core may be coated with a semipermeable membrane. Subsequently, the semipermeable membrane surrounding the core should be perforated with, for example, laser equipment.

The tablets of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein. A finish coat is generally water soluble or water erodible. The finish coat will plug a preformed passageway that has been formed just prior to application of the finish coat.

The pharmaceutical composition of the invention can be present as a manufactured batch or unit dose. The term "manufactured batch" is taken to mean any size batch of a composition containing the elements set forth herein but not yet included in a dosage form.

The pharmaceutical composition can be a homogeneous or heterogeneous mixture of the components therein. The pharmaceutical composition can comprise two different compositions, such as a first composition comprising oxybutynin and a second composition comprising the second drug. The first and second compositions can be stacked in the core of a solid dosage form or be in admixture or one of the first and second compositions can surround the other composition.

The method of the invention comprises the step of administering to a subject suffering from incontinence a dosage form or pharmaceutical composition comprising oxybutynin and a second drug. Alternatively, the method of the invention comprises the step of administering to a subject suffering from incontinence a dosage form or pharmaceutical composition comprising oxybutynin and another dosage form or pharmaceutical composition comprising a second drug.

The steps of the invention can comprise the steps of determining the pharmacokinetic, pharmacodynamic, pharmacological, therapeutic, behavioral and/or toxicological response of the subject to the system. These responses can be determined easily by those of ordinary skill in the art by monitoring the occurrence of side effects associated with the therapy, monitoring blood levels of drug, correlating blood levels of drug to particular formulations or patient profile, and/or observing improvement of urinary incontinence associated symptoms. When oxybutynin and the second drug are found in separate dosage forms, the dosage forms can be included in a kit.

The method of the invention can be adapted as follows. For frail elderly patients, lower dosages of drug will be required. For patients that respond poorly, i.e., receive a minimal therapeutic benefit from therapy, higher dosages will be required. For patients who exhibit side effects caused by drug, lower dosage will be required. For patients whose eating habits interfere with drug therapy, dosages can be adjusted according to observed plasma drug concentrations to provide the desired concentrations, i.e., undesirably low plasma drug concentrations are overcome by administering higher dosages of drug. If one particular embodiment of the invention is practiced on a mammal and unwanted side effects due to high plasma drug concentrations are observed, the system can be modified by changing the formulation(s) used such that the plasma level concentrations of the drugs are lower.

The kit is provided such that physicians and patients can easily determine the proper combination of first and second dosage forms that should be administered according to the above guiding principles. A start-up kit of the system is generally used as follows. An exemplary start-up kit comprises at least two first different tablets containing oxybutynin and at least two different tablets containing second drug. The physician administers and/or prescribes one formulation from each of the first and second tablets. After a period of time, usually one to fourteen days, the patient's response is determined. Depending upon the response, the physician may administer and/or prescribe different formulations for the first and/or second tablets. Where the patient exhibits accumulation of oxybutynin or the second drug, the physician may recommend lower dose first and/or second tablets, or use first or second tablets having a different release profile. Where the patient exhibits unwanted side effects during the initial part of each 24 hour period that the kit is administered, the physician may recommend lower dose controlled release tablets that provide lower initial plasma levels of the drugs. Where the patient exhibits a loss of therapeutic benefit during the latter part of each 24-hour period that the kit is administered, the physician may recommend tablets that release oxybutynin and/or the second drug over a longer period of time or that contain a higher dose of oxybutynin and/or second drug. When the first and second tablets are administered concurrently, they may be administered encased in a capsule, such as a hard or soft gelatin capsule. Alternatively, the first tablet can be a rapidly dissolving tablet that dissolves in the buccal cavity or a chewable tablet, while the second tablet is one that would be swallowed whole. Still, the first tablet could be a short acting controlled release tablet that begins to release oxybutynin shortly after administration while the second tablet is a conventional long acting delayed and controlled release tablet that begins to release the second drug at least three hours after administration.

The advantages of the present kit over known systems for treating oxybutynin include improved therapeutic benefit and/or reduced severity or occurrence of side effects.

The following examples should not be considered exhaustive, but merely illustrative of only a few of the many embodiments contemplated by the present invention. The methods described herein can be followed to prepare osmotic devices according to the invention.

EXAMPLE 1

The following procedure is used to prepare osmotic device formulations containing oxybutynin (2.5, 5 and 10 mg strength) and tolterodine (1 and 2 mg strength). The oxybutynin 15 and the tolterodine are located in separate stacked layers in the core of the osmotic device. The osmotic device formulations contain the following ingredients in the amounts indicated:

| | AMOUNT (mg) | AMOUNT (mg) | AMOUNT (mg) | AMOUNT (mg) |
|---|---|---|---|---|
| | | Oxybutynin Strength | | |
| | 5 | 5 | 10 | 2.5 |
| | | Tolterodine Strength | | |
| INGREDIENT | 1 | 2 | 2 | 2 |
| CORE | | | | |
| LAYER A | | | | |
| Oxybutynin Hydrochloride | 5.15 | 5.15 | 10.30 | 2.57 |
| Mannitol | 69.00 | 69.00 | 138.00 | 50.00 |
| Anhydrous Dextrose | 30.00 | 30.00 | 60.00 | 22.00 |
| Povidone | 6.35 | 6.35 | 12.70 | 15.30 |
| Polyethylene Glycol 400 | 1.15 | 1.15 | 2.30 | 1.23 |
| Polyethylene Glycol 6000 | 4.00 | 4.00 | 8.00 | 4.00 |
| Tartaric Acid | 2.00 | 2.00 | 4.00 | 2.20 |
| Magnesium Stearate | 1.35 | 1.35 | 2.70 | 1.70 |
| Colloidal Silicon Dioxide | 1.00 | 1.00 | 2.00 | 1.00 |
| LAYER B | | | | |
| Tolterodine L-Tartrate | 1.46 | 2.92 | 2.92 | 2.92 |
| Sodium Chloride | 50.00 | 50.00 | 50.00 | 50.00 |
| Microcrystalline cellulose | 78.54 | 77.08 | 77.08 | 77.08 |
| Povidone | 9.00 | 9.00 | 9.00 | 9.00 |
| Polyethylene Glycol 6000 | 5.00 | 5.00 | 5.00 | 5.00 |
| Polyethylene Glycol 400 | 2.00 | 2.00 | 2.00 | 2.00 |
| Red Ferric Oxide | 1.00 | 1.00 | 1.00 | 1.00 |
| Colloidal Silicon Dioxide | 1.00 | 1.00 | 1.00 | 1.00 |
| Magnesium Stearate | 2.00 | 2.00 | 2.00 | 2.00 |
| COATING A | | | | |
| Cellulose Acetate | 19.05 | 19.05 | 23.75 | 23.75 |
| Polyethylene Glycol 400 | 0.95 | 0.95 | 1.25 | 1.25 |
| COATING B | | | | |
| Hydroxypropyl methylcellulose 2910 | 3.70 | 3.70 | 5.55 | 5.55 |
| Copolyvidone | 3.00 | 3.00 | 1.58 | 1.58 |
| Polyethylene Glycol 6000 | 1.05 | 1.05 | 4.50 | 4.50 |
| Titanium Dioxide | 2.25 | 2.25 | 3.37 | 3.37 |

The oxybutynin composition is prepared by mixing oxybutynin HCl, povidone, mannitol, and anhydrous dextrose. The mixture is wet with a blend of polyethylene glycol 6000 and polyethylene glycol 400 in alcohol 96°. The blend is granulated and dried at 40-50° C. for 4 hours; then, it is screened and mixed with colloidal silicon dioxide and tartaric acid. The blend is mixed to homogeneity and magnesium stearate is added.

The tolterodine composition is prepared by mixing tolterodine L-tartrate sodium chloride, povidone, microcrystalline cellulose and red ferric oxide. The mixture is wet with a blend of polyethylene glycol 6000, and polyethylene glycol 400 in alcohol 96°. The blend is granulated and dried at 40-50° C. for 4 hours; then, it is screened and mixed with colloidal silicon dioxide. The blend is mixed to homogeneity and magnesium stearate is added.

The stacked core is prepared as follows. First, the oxybutynin composition is added to a punch die set, and tamped. Next, the tolterodine composition is added on top of the tamped oxybutynin and the two layers compressed using 8.50 mm diameter punches to form bi-layered cores.

A first composition to cover the core is prepared as follows: a mixture of cellulose acetate and polyethylene glycol 400 is added to a blend of acetone and methanol. This polymer mixture is sprayed onto the tablets in a conventional pan coater to obtain film-coated tablets.

The second coating is prepared by mixing hydroxypropyl methylcellulose 2910, polyethylene glycol 6000, copolyvidone, and titanium dioxide in a mixture of methylene chloride-alcohol 96° 70:30 (volume/volume). This polymer mixture is sprayed onto the final tablets in a conventional pan coater to obtain film-coated tablets. A 0.50 mm hole is drilled through the coating in each face of the tablet.

EXAMPLE 2

The procedure of Example 1 is used to prepare osmotic device formulations containing oxybutynin (5 and 10 mg strength) and darifenacin (5 and 10 mg strength) except that the formulations contain the following ingredients in the amounts indicated.

| | AMOUNT (mg) | AMOUNT (mg) |
|---|---|---|
| | Oxybutynin Strength | |
| | 5 | 10 |
| | Darifenacin Strength | |
| INGREDIENT | 10 | 5 |
| CORE | | |
| LAYER A | | |
| Oxybutynin Hydrochloride | 5.15 | 10.30 |
| Mannitol | 69.00 | 138.00 |
| Anhydrous Dextrose | 30.00 | 60.00 |
| Povidone | 6.35 | 12.70 |
| Polyethylene Glycol 400 | 1.15 | 2.30 |
| Polyethylene Glycol 6000 | 4.00 | 8.00 |
| Tartaric Acid | 2.00 | 4.00 |
| Magnesium Stearate | 1.35 | 2.70 |
| Colloidal Silicon Dioxide | 1.00 | 2.00 |
| LAYER B | | |
| Darifenacin Hydrobromide | 11.90 | 5.95 |
| Sodium Chloride | 52.00 | 98.05 |
| Microcrystalline cellulose | 76.10 | 68.00 |
| Povidone | 9.00 | 16.00 |
| Polyethylene Glycol 6000 | 5.00 | 5.50 |
| Polyethylene Glycol 400 | 2.00 | 4.00 |
| Red Ferric Oxide | 1.00 | 0.50 |
| Colloidal Silicon Dioxide | 1.00 | 1.00 |
| Magnesium Stearate | 2.00 | 1.00 |
| COATING A | | |
| Cellulose Acetate | 18.50 | 33.75 |
| Polyethylene Glycol 400 | 1.50 | 1.25 |

-continued

| INGREDIENT | AMOUNT (mg) Oxybutynin Strength 5 Darifenacin Strength 10 | AMOUNT (mg) Oxybutynin Strength 10 Darifenacin Strength 5 |
|---|---|---|
| COATING B | | |
| Hydroxypropyl methylcellulose 2910 | 3.70 | 5.55 |
| Copolyvidone | 3.00 | 1.58 |
| Polyethylene Glycol 6000 | 1.05 | 4.50 |
| Titanium Dioxide | 2.25 | 3.37 |

EXAMPLE 3

The following procedure is used to prepare osmotic devices comprising oxybutynin (5 or 10 mg strength) and darifenacin (5 or 10 mg strength) in the same composition. The oxybutynin and darifenacin composition is located in the core. The osmotic device formulation contain the following ingredients in the amounts indicated:

| INGREDIENT | AMOUNT (mg) Oxybutynin Strength 5 Darifenacin Strength 10 | AMOUNT (mg) Oxybutynin Strength 10 Darifenacin Strength 5 |
|---|---|---|
| CORE | | |
| Oxybutynin Hydrochloride | 5.15 | 10.30 |
| Darifenacin Hydrobromide | 11.90 | 5.95 |
| Mannitol | 119.35 | 240.35 |
| Anhydrous Dextrose | 91.50 | 183.00 |
| Povidone | 8.50 | 17.00 |
| Polyethylene Glycol 400 | 2.00 | 4.00 |
| Polyethylene Glycol 6000 | 4.00 | 8.00 |
| Tartaric Acid | 2.60 | 5.20 |
| Colloidal Silicon Dioxide | 2.00 | 4.00 |
| Magnesium Stearate | 3.00 | 6.00 |
| COATING A | | |
| Cellulose Acetate | 23.35 | 28.85 |
| Polyethylene Glycol 400 | 1.65 | 1.15 |
| COATING B | | |
| Opadry 1 | 10.00 | 15.00 |
| Purified water | 73.00 | 110.00 |

The core composition is prepared by mixing: oxybutynin HCl, darifenacin HBr, povidone, mannitol, and anhydrous dextrose. The mixture is wet with a blend of polyethylene glycol 6000 and polyethylene glycol 400 in alcohol 96°. The blend is granulated and dried at 40-50° C. for 4 hours; then, it is screened and mixed with colloidal silicon dioxide and tartaric acid. The blend is mixed to homogeneity magnesium stearate is added. This final blend is tabletted using biconcave 8.0 mm diameter punches.

A first composition to cover the cores is prepared as follows: cellulose acetate and polyethylene glycol 400 are added to a blend of acetone and methanol. This polymer mixture is sprayed onto the tablets in a conventional pan coater to obtain film-coated tablets. A 0.50 mm hole is drilled through the coating of the tablet.

The second coating is prepared by mixing Opadry in purified water. This polymer mixture is sprayed onto the final tablets in a conventional pan coater to obtain film-coated tablets.

EXAMPLE 4

The procedure of Example 3 is used to prepare osmotic device formulations containing oxybutynin (2.5, 5 and 10 mg strength) and tolterodine L-tartrate (1 or 2 mg strength) except that the formulations contain the following ingredients in the amounts indicated.

| INGREDIENT | AMOUNT (mg) Oxybutynin Strength 5 Tolterodine Strength 1 | AMOUNT (mg) Oxybutynin Strength 5 Tolterodine Strength 2 | AMOUNT (mg) Oxybutynin Strength 10 Tolterodine Strength 2 | AMOUNT (mg) Oxybutynin Strength 2.5 Tolterodine Strength 2 |
|---|---|---|---|---|
| CORE | | | | |
| Oxybutynin Hydrochloride | 5.15 | 5.15 | 10.30 | 2.57 |
| Tolterodine L-tartrate | 1.46 | 2.92 | 2.92 | 2.92 |
| Mannitol | 85.00 | 85.00 | 170.00 | 169.73 |
| Anhydrous Dextrose | 178.54 | 177.08 | 355.08 | 355.08 |
| Povidone | 9.00 | 9.00 | 18.00 | 18.00 |
| Polyethylene Glycol 4000 | 5.00 | 5.00 | 10.00 | 10.00 |
| Polyethylene Glycol 400 | 2.00 | 2.00 | 4.00 | 4.00 |
| Colloidal Silicon Dioxide | 1.00 | 1.00 | 2.00 | 2.00 |
| Magnesium Stearate | 2.85 | 2.85 | 5.70 | 5.70 |
| COATING A | | | | |
| Cellulose Acetate | 23.05 | 23.05 | 30.25 | 21.25 |
| Polyethylene Glycol 400 | 1.95 | 1.95 | 1.75 | 0.75 |
| COATING B | | | | |
| Opadry 1 | 10.00 | 10.00 | 15.00 | 15.00 |
| Purified water | 73.00 | 73.00 | 110.00 | 110.00 |

EXAMPLE 5

The following procedure is used to prepare controlled release matrix tablets formulations containing oxybutynin (2.5, 5 or 10 mg strength) and tolterodine L-tartrate (1 or 2 mg strength) in the same composition.

| INGREDIENT | AMOUNT (mg) Oxybutynin Strength 5 Tolterodine Strength 1 | AMOUNT (mg) Oxybutynin Strength 5 Tolterodine Strength 2 | AMOUNT (mg) Oxybutynin Strength 10 Tolterodine Strength 2 | AMOUNT (mg) Oxybutynin Strength 2.5 Tolterodine Strength 2 |
|---|---|---|---|---|
| CORE | | | | |
| Oxybutynin Hydrochloride | 5.15 | 5.15 | 10.30 | 2.57 |
| Tolterodine l-tartrate | 1.46 | 2.92 | 2.92 | 2.92 |
| Lactose DT | 71.24 | 70.78 | 142.48 | 142.21 |
| HPMC 2208 (4,000 cps) | 106.30 | 106.30 | 212.60 | 212.60 |
| Tartaric Acid | 2.00 | 2.00 | 4.00 | 4.00 |

-continued

|  | AMOUNT (mg) | AMOUNT (mg) | AMOUNT (mg) | AMOUNT (mg) |
|---|---|---|---|---|
|  | Oxybutynin Strength | | | |
|  | 5 | 5 | 10 | 2.5 |
|  | | Tolterodine Strength | | |
| INGREDIENT | 1 | 2 | 2 | 2 |
| Colloidal Silicon Dioxide | 1.90 | 1.90 | 3.80 | 3.80 |
| Magnesium Stearate | 0.95 | 0.95 | 1.90 | 1.90 |
| COATING A | | | | |
| Opadry 1 | 10.00 | 10.00 | 10.00 | 10.00 |
| Purified water | 73.00 | 73.00 | 73.00 | 73.00 |

The core composition is prepared by mixing oxybutynin HCl, tolterodine L-tartrate, lactose DT, and HPMC 2208 for 10 minutes. Then, the mixture is screened and mixed with colloidal silicon dioxide and tartaric acid. The blend is mixed to homogeneity and magnesium stearate is added. The final blend is tabletted using biconcave 8.0 mm diameter punches.

The coating is prepared by mixing Opadry 1 in purified water. The polymer mixture is sprayed onto the final tablets in a conventional pan coater to obtain film-coated tablets.

EXAMPLE 6

The procedure of Example 5 is used to prepare controlled release matrix tables formulations containing oxybutynin (5 or 10 mg strength) and darifenacin (5 or 10 mg strength) in the same composition except that the formulations contain the following ingredients in the amounts indicated.

|  | AMOUNT (mg) | AMOUNT (mg) |
|---|---|---|
|  | Oxybutynin Strength | |
|  | 5 | 10 |
|  | Darifenacin Strength | |
| INGREDIENT | 10 | 5 |
| CORE | | |
| Oxybutynin Hydrochloride | 5.15 | 10.30 |
| Darifenacin Hydrobromide | 11.90 | 5.95 |
| Cellactose | 84.10 | 170.05 |
| HPMC 2208 (4,000) | 142.50 | 285.00 |
| Tartaric Acid | 2.60 | 5.20 |
| Colloidal Silicon Dioxide | 2.50 | 5.00 |
| Magnesium Stearate | 1.25 | 2.50 |
| COATING A | | |
| Opadry 1 | 10.00 | 15.00 |
| Purified water | 73.00 | 110.00 |

EXAMPLE 7

Bi-Layered Controlled Release Tablet

These tablets provide a sustained delivery of oxybutynin for at least a period of about 8 hours and a rapid delivery of darifenacin in the colon.

|  | AMOUNT (mg) | AMOUNT (mg) |
|---|---|---|
|  | Oxybutynin Strength | |
|  | 5 | 10 |
|  | Darifenacin Strength | |
| INGREDIENT | 10 | 5 |
| LAYER A | | |
| Oxybutynin Hydrochloride | 5.15 | 10.30 |
| Myvacet 5-07 | 10.80 | 10.80 |
| Povidone K25 | 5.40 | 5.40 |
| Microcrystalline Cellulose Spheres | 68.68 | 63.53 |
| Cellulose Acetophtalate | 4.10 | 4.10 |
| Colloidal Silicon Dioxide | 0.60 | 0.60 |
| Croscarmellose Sodium | 1.80 | 1.80 |
| Magnesium Stearate | 10.80 | 10.80 |
| LAYER B | | |
| Darifenacin Hydrobromide | 11.90 | 5.95 |
| Guar Gum | 52.07 | 52.07 |
| Red Iron Oxide | 0.15 | 0.15 |
| Microcrystalline Cellulose Spheres | 68.68 | 74.63 |
| Eudragit | 4.59 | 4.59 |
| Colloidal Silicon Dioxide | 0.60 | 0.60 |
| Croscarmellose Sodium | 1.80 | 1.80 |
| Magnesium Stearate | 10.80 | 10.80 |

The oxybutynin composition is prepared as follows. Myvacet 5-07 is dissolved along with oxybutynin HCl and PVP K 25. This mixture is then applied onto microcrystalline cellulose spheres. These microgranules are coated with a coat comprising cellulose acetophtalate.

The darifenacin composition is prepared as follows. Guar gum is dissolved in an appropriate reactor along with red iron oxide. Darifenacin HBr is added and thoroughly mixed. This mixture is then applied on microcrystalline cellulose spheres. Next, these microgranules are coated with a coat comprising Eudragit L.

Both compositions are thoroughly mixed with colloidal silicon dioxide, croscarmellose and magnesium stearate and compressed in a suitable rotary tablet machine to make bilayer tablets.

EXAMPLE 8

Bi-Layered Controlled Release Tablet

These tablets provide a sustained delivery of oxybutynin and tolterodine for a period of at least about 7 hours.

|  | AMOUNT (mg) | AMOUNT (mg) |
|---|---|---|
|  | Oxybutynin Strength | |
|  | 5 | 10 |
|  | Tolterodine Strength | |
| INGREDIENT | 2 | 2 |
| LAYER A | | |
| Oxybutynin Hydrochloride | 5.15 | 10.30 |
| Myvacet 5-07 | 10.80 | 10.80 |
| Povidone K25 | 5.40 | 5.40 |
| Microcrystalline Cellulose Spheres | 68.68 | 63.53 |
| Cellulose Acetophtalate | 4.10 | 4.10 |

-continued

|  | AMOUNT (mg) | AMOUNT (mg) |
|---|---|---|
|  | Oxybutynin Strength | |
|  | 5 | 10 |
|  | Tolterodine Strength | |
| INGREDIENT | 2 | 2 |
| Colloidal Silicon Dioxide | 0.60 | 0.60 |
| Croscarmellose Sodium | 1.80 | 1.80 |
| Magnesium Stearate | 10.80 | 10.80 |
| LAYER B | | |
| Tolterodine L-tartrate | 2.92 | 2.92 |
| Myvaplex 600P NF | 82.07 | 82.07 |
| Red Iron Oxide | 0.15 | 0.15 |
| Microcrystalline Cellulose Spheres | 67.76 | 67.76 |
| Cellulose Acetophtalate | 4.10 | 4.10 |
| Colloidal Silicon Dioxide | 0.60 | 0.60 |
| Croscarmellose Sodium | 1.80 | 1.80 |
| Magnesium Stearate | 0.75 | 0.75 |

The oxybutynin composition is prepared as follows. Myvacet 5-07 is dissolved along with oxybutynin HCl and PVP K 25. This mixture is then applied onto microcrystalline cellulose spheres. These microgranules are coated with a coat comprising cellulose acetophtalate.

The tolterodine composition is prepared as follows. Myvaplex 600P NF is hot melted in an appropriate reactor supplied with a heating chamber along with red iron oxide. Tolterodine L-tartrate is added and thoroughly mixed. This mixture is then applied on microcrystalline cellulose spheres. Next, these microgranules are coated with a coat comprising cellulose acetophthalate.

Both compositions are thoroughly mixed with colloidal silicon dioxide, croscarmellose and magnesium stearate and compressed in a suitable rotary tablet machine to make bi-layered tablets.

EXAMPLE 9

Rapid Release Tablets

These tablets release about 80% of their oxybutynin and tolterodine charge rapidly within about 0.5 hours after administration. These tablets maintain therapeutically effective levels of oxybutynin and tolterodine in a mammal for a period of up to about 3 hours after administration. This exemplary tablet releases oxybutynin and tolterodine for a period of up to about 0.5-3.0 hours after administration.

|  | AMOUNT (mg) | AMOUNT (mg) |
|---|---|---|
|  | Oxybutynin Strength | |
|  | 5 | 10 |
|  | Tolterodine Strength | |
| INGREDIENT | 2 | 2 |
| Oxybutynin Hydrochloride | 5.15 | 10.30 |
| Tolterodine L-tartrate | 2.92 | 2.92 |
| Monohydrate Lactose | 116.23 | 111.23 |
| Microcrystalline cellulose | 36.50 | 36.35 |
| Povidone | 5.40 | 5.40 |
| Colloidal Silicon Dioxide | 1.20 | 1.20 |

-continued

|  | AMOUNT (mg) | AMOUNT (mg) |
|---|---|---|
|  | Oxybutynin Strength | |
|  | 5 | 10 |
|  | Tolterodine Strength | |
| INGREDIENT | 2 | 2 |
| Aluminum Lake Brilliant Blue | 0.15 | 0.15 |
| Croscarmellose Sodium | 3.60 | 3.60 |
| Magnesium Stearate | 1.50 | 1.50 |
| Sodium Lauryl Sulfate | 3.50 | 3.50 |

The tablet composition is prepared by mixing oxybutynin, tolterodine L-tartrate, lactose, and microcrystalline cellulose. Aluminum lake brilliant blue previously screened through a 200 mesh is added to the mixture. Then, the blend is granulated with PVP in 96° ethanol and the final granulate is dried in a fluid bed dryer. The granulated composition is passed through a 50 mesh and blended with croscarmellose sodium, magnesium stearate and sodium lauryl sulfate. The final blend is then subjected to compression on a tabletting machine.

EXAMPLE 10

Immediate release tablets

The tablets of this example are made as follows. The tablets include exemplary formulations for the different individual types of tablets.

(a) Effervescent Tablets

|  | AMOUNT (mg) | AMOUNT (mg) |
|---|---|---|
|  | Oxybutynin Strength | |
|  | 5 | 10 |
|  | Tolterodine Strength | |
| INGREDIENT | 2 | 2 |
| Oxybutynin Hydrochloride | 5.15 | 10.30 |
| Tolterodine L-tartrate | 2.92 | 2.92 |
| Sorbitol | 415.00 | 409.85 |
| Citric Acid | 240.00 | 240.00 |
| Sodium Bicarbonate | 115.00 | 115.00 |
| Polyethylene Glycol 6000 | 18.00 | 18.00 |
| Orange flavor | 3.48 | 3.48 |
| Saccharin Sodium | 0.44 | 0.44 |

Effervescent tablets containing oxybutynin and tolterodine are prepared as follows. Oxybutynin HCl, tolterodine L-tartrate, sorbitol, citric acid, sodium bicarbonate (dried during 2 hours at 105° C.), polyethylene glycol 6000, orange flavor and saccharin sodium are mixed. This mixture is screened and then tabletted at a maximum 25% relative atmospheric humidity, using biplanar 14.0-mm diameter punches.

(b) Chewable Tablets

|  | AMOUNT (mg) | AMOUNT (mg) |
|---|---|---|
|  | Oxybutynin Strength | |
|  | 5 | 10 |
|  | Tolterodine Strength | |
| INGREDIENT | 2 | 2 |
| Oxybutynin Hydrochloride | 5.15 | 10.30 |
| Tolterodine L-tartrate | 2.92 | 2.92 |
| Microcrystalline Cellulose | 273.39 | 268.24 |
| Sorbitol | 140.00 | 140.00 |
| Dextrose | 54.50 | 54.50 |
| Poly(ethylene glycol) 6000 | 12.00 | 12.00 |
| Colloidal Silicon Dioxide | 1.50 | 1.50 |
| Magnesium Stearate | 4.20 | 4.20 |
| Strawberry flavor | 5.80 | 5.80 |
| Saccharin Sodium | 0.54 | 0.54 |

Chewable tablets containing oxybutynin and tolterodine are prepared as follows. Oxybutynin HCl, tolterodine L-tartrate, sorbitol, microcrystalline cellulose, dextrose, polyethylene glycol 6000, strawberry flavor and saccharin sodium are mixed. This mixture is screened, and then blended with colloidal silicon dioxide and magnesium stearate. The blend is tabletted using biplanar 10.0-mm diameter punches.

(c) Very Rapidly Dissolving Tablets

|  | AMOUNT (mg) | AMOUNT (mg) |
|---|---|---|
|  | Oxybutynin Strength | |
|  | 5 | 10 |
|  | Tolterodine Strength | |
| INGREDIENT | 2 | 2 |
| Oxybutynin Hydrochloride | 5.15 | 10.30 |
| Tolterodine L-tartrate | 2.92 | 2.92 |
| Microcrystalline Cellulose | 12.08 | 6.93 |
| Sorbitol | 15.40 | 15.40 |
| Crospovidone | 13.55 | 13.55 |
| Magnesium Stearate | 0.25 | 0.25 |
| Orange flavor | 0.60 | 0.60 |
| Saccharin Sodium | 0.05 | 0.05 |

Very rapidly dissolving tablets containing oxybutynin and tolterodine are prepared as follows. Oxybutynin HCl, sorbitol, microcrystalline cellulose, crospovidone, orange flavor and saccharin sodium are mixed. Next, the mixture is screened and then mixed with magnesium stearate. Finally the blend is tabletted using biconcave 5.0-mm diameter punches.

EXAMPLE 11

Oxybutynin-Darifenacin Vaginal Cream

Amount per 5 g dose

| Ingredient | Amount |
|---|---|
| Oxybutynin Hydrochloride | 0.05 |
| Darifenacin hydrobromide | 0.02 |
| Polyethylene Glycol 1000 | 0.09 |

-continued

| Ingredient | Amount |
|---|---|
| Monocetyl Ether Cetostearyl Alcohol | 0.30 |
| Mineral Oil | 0.30 |
| White Petrolatum | 0.72 |
| Propyl paraben | 0.004 |
| Methyl paraben | 0.0075 |
| Benzyl Alcohol | 0.075 |
| Purified Water | 3.4085 |

Oxybutynin HCl, darifenacin HBr, methyl and propyl paraben and benzyl alcohol are dissolved in warm water. The polyethylene glycol 1000, monocetyl ether cetostearyl alcohol, mineral oil and white petrolatum are melted together on a hot water bath. The aqueous solution is added to the molten oils and stirred until cold.

EXAMPLE 12

Oxybutynin-Darifenacin Osmotic Device

The procedure of Example 1 is used to prepare osmotic device formulations containing oxybutynin (5 and 10 mg strength) and darifenacin (5 and 10 mg strength) except that the formulations contain the following ingredients in the amounts indicated.

|  | AMOUNT (mg) | AMOUNT (mg) |
|---|---|---|
|  | Oxybutynin Strength | |
|  | 5 | 10 |
|  | Darifenacin Strength | |
| INGREDIENT | 10 | 5 |
| CORE LAYER A | | |
| Oxybutynin Hydrochloride | 5.15 | 10.30 |
| Mannitol | 69.00 | 138.00 |
| Anhydrous Dextrose | 30.00 | 60.00 |
| Povidone | 6.35 | 12.70 |
| Polyethylene Glycol 400 | 1.15 | 2.30 |
| Polyethylene Glycol 6000 | 4.00 | 8.00 |
| Tartaric Acid | 2.00 | 4.00 |
| Magnesium Stearate | 1.35 | 2.70 |
| Colloidal Silicon Dioxide | 1.00 | 2.00 |
| LAYER B | | |
| Darifenacin Hydrobromide | 11.90 | 5.95 |
| Hydroxypropylmethylcellulose 2208 (4,000) | 91.20 | 173.28 |
| Cellactose | 53.15 | 117.27 |
| Magnesium Stearate | 2.50 | 5.00 |
| Colloidal Silicon Dioxide | 1.25 | 2.50 |
| COATING A | | |
| Cellulose Acetate | 18.50 | 33.75 |
| Polyethylene Glycol 400 | 1.50 | 1.25 |
| COATING B | | |
| Hydroxypropylmethylcellulose 2910 | 3.70 | 5.55 |
| Copolyvidone | 3.00 | 1.58 |
| Polyethylene Glycol 6000 | 1.05 | 4.50 |
| Titanium Dioxide | 2.25 | 3.37 |

Those of skill in the art should, in light of the present disclosure, appreciate that many changes can be made in the specific embodiments that are disclosed herein and still obtain a like or similar result without departing from the spirit and scope of the invention. All of the compositions and methods disclosed and claimed herein can be made and executed without undue experimentation in light of the present disclosure.

We claim:

1. A dual controlled release osmotic device consisting essentially of:
   a bi-layered core consisting essentially of a controlled release active agent-containing first layer and a controlled release active agent-containing second layer, wherein the first and second layers are in intimate contact with one another and in stacked arrangement, and the osmotic device excludes a partition between the first layer and the second layer and excludes a push-layer; and
   a membrane enveloping the core, wherein the membrane comprises at least one preformed passageway in communication with at least one of the first and second active agent-containing layers;
   whereby the osmotic device provides a controlled release of the first active agent through at least one preformed passageway according to a first release profile and the second layer provides a controlled release of the second active agent through at least one preformed passageway according to a second release profile.

2. The osmotic device of claim 1, wherein the osmotic device comprises at least one first preformed passageway in communication with the first layer and at least one second preformed passageway in communication with the second layer.

3. The osmotic device of claim 2, wherein at least one of the two preformed passageways is plugged with a water soluble and/or water erodible material.

4. The osmotic device of claim 2, wherein both of the preformed passageways are plugged with a water soluble and/or water erodible material, and the material plugging the first passageway is the same as the material plugging the second passageway.

5. The osmotic device of claim 2, wherein both of the preformed passageways are plugged with a water soluble and/or water erodible material, and the material plugging the first passageway is different than the material plugging the second passageway.

6. The osmotic device of claim 1, wherein the membrane comprises at least one preformed passageway in communication with both the first and second layers.

7. The osmotic device of claim 1 further comprising at least one external coat exterior to the membrane.

8. The osmotic device of claim 7, wherein the external coat is independently selected at each occurrence from water soluble and/or water erodible.

9. The osmotic device of claim 7, wherein the external coat is independently selected at each occurrence from microporous, permeable, semipermeable and impermeable.

10. The osmotic device of claim 7, wherein the external coat is independently selected at each occurrence from inert and drug-containing.

11. The osmotic device of claim 10, wherein the external coat provides a rapid release of drug.

12. The osmotic device of claim 7, wherein the membrane comprises at least a first preformed passageway and at least a second preformed passageway, wherein the first passageway has been formed after application of the external coat to the membrane, and the second passageway has been formed before application of the external coat to the membrane such that the second passageway is plugged by the external coat, and release of the second active agent begins after release of the first active agent has started.

13. The osmotic device of claim 7, wherein the membrane comprises at least a first preformed passageway and at least a second preformed passageway, wherein the first and second passageways have been formed before application of the external coat to the membrane; and the first and second passageways are plugged by the external coat.

14. The osmotic device of claim 1 further comprising at least one internal coat interposed the core and the membrane.

15. The osmotic device of claim 14, wherein the internal coat is independently selected at each occurrence from water soluble and/or water erodible.

16. The osmotic device of claim 14, wherein the internal coat is independently selected at each occurrence from inert and drug-containing.

17. The osmotic device of claim 14, wherein the internal coat is independently selected at each occurrence from microporous, permeable, semipermeable and impermeable.

18. The osmotic device of claim 1, wherein the first active agent and the second active agent are released from the core sequentially or in an overlapping manner when the osmotic device is exposed to an aqueous environment.

19. The osmotic device of claim 1, wherein each active agent is independently released from the core according to a timed, targeted, pseudo-first order, first order, pseudo-zero order, zero-order, sustained, slow, extended, pulsatile and/or delayed release profile.

20. The osmotic device of claim 1, wherein initial release of the first active agent and the second active agent is delayed for a period of time after exposure to an aqueous environment.

21. The osmotic device of claim 20, wherein each active agent is independently released from the core according to a timed, targeted, pseudo-first order, first order, pseudo-zero order, zero-order, sustained, slow, extended, and/or pulsatile release profile.

22. The osmotic device of claim 1 comprising:
    a bi-layered core consisting essentially of a controlled release first layer comprising a first drug and at least one pharmaceutical excipient, and a different controlled release second layer comprising a second drug and at least one pharmaceutical excipient, wherein the first and second layers are in intimate contact with one another and in stacked arrangement, and the core excludes a partition between the first layer and the second layer and excludes a push-layer; and
    a membrane enveloping the core and having at least two preformed passageways to permit a controlled release of the first and second drugs from the core when the osmotic device is exposed to an aqueous environment, wherein at least one first passageway is in communication with the first layer and at least one second passageway is in communication with the second layer.

23. The osmotic device of claim 22, wherein the membrane is semipermeable.

24. The osmotic device of claim 22, wherein each drug is independently released from the core according to a timed, targeted, pseudo-first order, first order, pseudo-zero order, zero-order, sustained, slow, extended, pulsatile and/or delayed release profile.

25. The osmotic device of claim 22, wherein the first drug and the second drug are released from the core sequentially or in an overlapping manner when the osmotic device is exposed to an aqueous environment.

26. The osmotic device of claim 22 further comprising at least one external coat exterior to the membrane.

27. The osmotic device of claim 26, wherein the external coat is independently selected at each occurrence from water soluble and/or water erodible.

28. The osmotic device of claim 26, wherein the external coat is independently selected at each occurrence from microporous, permeable, semipermeable and impermeable.

29. The osmotic device of claim 26, wherein the external coat is independently selected at each occurrence from inert and drug-containing.

30. The osmotic device of claim 29, wherein the external coat provides a rapid release of drug.

31. The osmotic device of claim 26, wherein the first passageway has been formed after application of the external coat to the semipermeable membrane and the second passageway has been formed before application of the external coat to the semipermeable membrane such that the second passageway is plugged by the external coat and release of the second drug begins after release of the first drug has started.

32. The osmotic device of claim 26, wherein the first and second passageways have been formed before application of the external coat to the semipermeable membrane; the first and second passageways are plugged by the external coat; and release of the first drug and the second drug is delayed for a period of time after exposure to an aqueous environment.

33. The osmotic device of claim 22 further comprising at least one internal coat interposed the core and the membrane.

34. The osmotic device of claim 33, wherein the internal coat is independently selected at each occurrence from water soluble and/or water erodible.

35. The osmotic device of claim 33, wherein the internal coat is independently selected at each occurrence from inert and drug-containing.

36. The osmotic device of claim 33, wherein the internal coat is independently selected at each occurrence from microporous, permeable, semipermeable and impermeable.

37. The osmotic device of claim 22, wherein the first drug and the second drug are released sequentially or in an overlapping manner when the osmotic device is exposed to an aqueous environment.

38. The osmotic device of claim 1 comprising:
a bi-layered core consisting essentially of a controlled release active agent-containing first layer and a controlled release active agent-containing second layer, wherein the first and second layers are in intimate contact with one another, and the layers are in stacked arrangement, and the core excludes a partition between the first layer and the second layer and excludes a push-layer; and
a semipermeable membrane enveloping the core, wherein the membrane comprises at least one preformed passageway in communication with at least one of the first and second active agent-containing layers;
whereby the osmotic device provides a controlled release of the first active agent through at least one preformed passageway according to a first release profile and the second layer provides a controlled release of the second active through at least one preformed passageway according to a second release profile, and each drug is independently released from the core according to a timed, targeted, pseudo-first order, first order, pseudo-zero order, zero-order, sustained, slow, extended, pulsatile and/or delayed release profile.

39. The osmotic device of claim 38 further comprising at least one external coat exterior to the membrane.

40. The osmotic device of claim 39, wherein the external coat is independently selected at each occurrence from water soluble and/or water erodible.

41. The osmotic device of claim 39, wherein the external coat is independently selected at each occurrence from microporous, permeable, semipermeable and impermeable.

42. The osmotic device of claim 39, wherein the external coat is independently selected at each occurrence from inert and drug-containing.

43. The osmotic device of claim 42, wherein the external coat provides a rapid release of drug.

44. The osmotic device of claim 39, wherein the first passageway has been formed after application of the external coat to the semipermeable membrane and the second passageway has been formed before application of the external coat to the semipermeable membrane such that the second passageway is plugged by the external coat and release of the second active agent begins after release of the first active agent has started.

45. The osmotic device of claim 39, wherein the first and second passageways have been formed before application of the external coat to the semipermeable membrane; the first and second passageways are plugged by the external coat; and release of the first active agent and the second active agent is delayed for a period of time after exposure to an aqueous environment.

46. The osmotic device of claim 38 further comprising at least one internal coat interposed the core and the membrane.

47. The osmotic device of claim 46, wherein the internal coat is independently selected at each occurrence from water soluble and/or water erodible.

48. The osmotic device of claim 46, wherein the internal coat is independently selected at each occurrence from microporous, permeable, semipermeable and impermeable.

49. The osmotic device of claim 46, wherein the internal coat is independently selected at each occurrence from inert and drug-containing.

50. The osmotic device of claim 38, wherein the first active agent and the second active agent are released sequentially or in an overlapping manner when the osmotic device is exposed to an aqueous environment.

51. The osmotic device of claim 1, 22 or 38, wherein the first release profile and the second release profile are different.

* * * * *